(12) United States Patent
Andersson et al.

(10) Patent No.: US 9,278,119 B2
(45) Date of Patent: Mar. 8, 2016

(54) TREATMENT OF PROSTATE CANCER AND A METHOD FOR DETERMINING THE PROGNOSIS FOR PROSTATE CANCER PATIENTS

(75) Inventors: Tommy Andersson, Malmö (SE); Anders Bjartell, Malmö (SE)

(73) Assignee: WNTRESEARCH AB, Malmö (SE)

( * ) Notice: Subject to any disclaimer, the term of this patent is extended or adjusted under 35 U.S.C. 154(b) by 0 days.

(21) Appl. No.: 14/128,064

(22) PCT Filed: Jun. 28, 2012

(86) PCT No.: PCT/SE2012/050738
§ 371 (c)(1),
(2), (4) Date: Feb. 3, 2014

(87) PCT Pub. No.: WO2013/006129
PCT Pub. Date: Jan. 10, 2013

(65) Prior Publication Data
US 2014/0206623 A1    Jul. 24, 2014

(30) Foreign Application Priority Data
Jul. 1, 2011    (SE) .................................. 1150619-3

(51) Int. Cl.
| | |
|---|---|
| A61K 38/04 | (2006.01) |
| C07K 7/00 | (2006.01) |
| A61P 35/00 | (2006.01) |
| A61K 38/10 | (2006.01) |
| C07K 14/475 | (2006.01) |
| G01N 33/50 | (2006.01) |
| G01N 33/574 | (2006.01) |
| A61K 38/08 | (2006.01) |

(52) U.S. Cl.
CPC ................ *A61K 38/10* (2013.01); *A61K 38/08* (2013.01); *C07K 14/475* (2013.01); *G01N 33/5088* (2013.01); *G01N 33/57434* (2013.01); *G01N 2800/52* (2013.01)

(58) Field of Classification Search
CPC ............ C07K 14/475; G01N 33/5088; G01N 2800/52; G01N 33/57434; A61K 38/10; A61K 38/08
See application file for complete search history.

(56) References Cited

U.S. PATENT DOCUMENTS

| | | | |
|---|---|---|---|
| 4,840,967 | A | 6/1989 | Beeley et al. |
| 7,238,709 | B2 | 7/2007 | Mammen et al. |
| 7,247,426 | B2 | 7/2007 | Yakhini et al. |
| 8,497,352 | B2 | 7/2013 | Andersson |
| 2007/0224201 | A1 | 9/2007 | Wu et al. |
| 2008/0207521 | A1 | 8/2008 | Andersson |

FOREIGN PATENT DOCUMENTS

| | | |
|---|---|---|
| EP | 1 033 405 A2 | 9/2000 |
| WO | WO-98/23730 A1 | 6/1998 |
| WO | WO-00/31261 A2 | 6/2000 |
| WO | WO-01/32708 A1 | 5/2001 |
| WO | WO-2006/130082 A1 | 12/2006 |
| WO | WO-2009/134204 A1 | 11/2009 |
| WO | WO-2010/019103 A1 | 2/2010 |
| WO | WO-2012/109540 A1 | 8/2012 |

OTHER PUBLICATIONS

Rudinger, Peptide Hormones, JA Parsons, Ed., 1976, pp. 1-7.*
SIGMA, 2004, pp. 1-2.*
Berendsen, A Glimpse of the Holy Grail?, Science, 1998, 282, pp. 642-643.*
Voet et al, Biochemistry, John Wiley & Sons Inc., 1995, pp. 235-241.*
Ngo et al, Computational Complexity, Protein Structure Protection, and the Levinthal Paradox, 1994, pp. 491-494.*
Bradley et al., Limits of Cooperativity in a Structurally Modular Protein: Response of the Notch Ankyrin Domain to Analogous Alanine Substitutions in Each Repeat, J. Mol. BIoL (2002) 324, 373-386.*
Santiago-Walker et al, The Ups and Downs of Transcription Factors in Melanoma, JNCI, 2010, 102, pp. 1103-1104.*
Pukrop, T., et al. "The complex pathways of Wnt-5a in cancer progression", (2008) *J. Mol Med*, 86(3):259-266.
Anderson, "Protease-activated receptor 1 is the primary mediator of thrombin-stimulated platelet procoagulant activity" (1999) *Proc. Natl. Acad. Sci. USA*, 96: 11189-11103.
Berney, D.M., et al. "Ki-67 and outcone in clinically localised prostate cancer: analysis of conservatively treated prostate cancer patients from the Trans-Atlantic Prostate Group study" (2009) *British Journal of Cancer*, 100: 888-893.
Bittner, M., et al. "molecular classification of cutaneous malignant melanoma by gene expression profiling" (2000) *Nature*, 406(6795): 536-540.
Blanc, E., et al. "Low expression of Wnt-5a gene is associated with high-risk neuroblastoma" (2005) *Oncogene*, 24: 1277-1283.
Cadigan, K.M., et al. "Wnt signaling: a common theme in animal development" (1997) *Genes & Development*, 11: 3286-3305.
Chen, C.D., et al. "Molecular determinants of resistance to antiandrogen therapy" (2003) *Nature Medicine*, 10(1): 33-39.

(Continued)

*Primary Examiner* — Julie Ha
*Assistant Examiner* — Li Ni Komatsu
(74) *Attorney, Agent, or Firm* — Harness, Dickey and Pierce, P.L.C.

(57) ABSTRACT

The present invention relates to a Wnt5a protein or peptide thereof possessing Wnt5a signaling properties, such as Foxy5, for use in the treatment of prostate cancer, in particular in patients that have undergone or will undergo radical prosteatectomy. The invention also relates to a method for determining a prognosis for a patient having prostate cancer and a kit for performing said method. The method for determining a prognosis for a patient comprises the steps of: evaluating an amount of Wnt5a protein present in at least part of a sample earlier obtained from the patient and determining a sample value corresponding to the evaluated amount; comparing the sample value obtained in step a) with a reference value associated with a reference prognosis; and, if said sample value is higher than said reference value, concluding that the prognosis for said patient is better than said reference prognosis.

7 Claims, 6 Drawing Sheets

(56) References Cited

OTHER PUBLICATIONS

Chen, G., et al. "Up-regulation of Wnt-1 and β-Catenin production in patients with advanced metastatic prostate carcinoma: potential pathogenic and prognostic implications" (2004) *Cancer*, 101:1345-1356.

Chesire, D.R., et al. "In vitro evidence for complex modes of nuclear β-Catenin signaling during prostate growth and tumorigenesis" (2002) *Oncogene*, 21:2679-2694.

Chien, A.J., et al. "Activated Ent/β-Catenin signaling in melanoma is associated with decreased proliferation in patient tumors and a murine melanoma model" (2009) *PNAS*, 106(4):1193-1198.

Da Forno, P.D., et al. "WNT5A expression increases during melanoma progression and correlates with outcome" (2008) *Clinical Cancer Research*, 14(18): 5825-5832.

Debes, J.D., et al. "Mechanisms of androgen-refratory prostate cancer" (2004) *New England Journal of Medicine*, 351(15):1488-1490.

Deimek, et al. "WNT-5 and G-protein signaling are required for collagen-induced DDR1 receptor activation and normal mammary Cell adhesion" (2003) 103: 344-351.

Dejmek, J., et al. "Expression and signaling activity of Wnt-5a/discoidin domain receptor-1 and Syk plays distinct but decisive roles in breast cancer patient survival" (2005) 11(2 pt 1): 520-528.

Dejmek, J., et al. "Wnt-5a protein expression in primary dukes B colon cancers indentifies a subgroup of patients with good prognosis" (2005) *Cancer Res*. 65(20): 9142-9146.

Derian, C.K., et al., "Selective inhibition of N-formylpeptide-induced neutrophil activation by carbamate-modified peptide analogues" (1996) *Biochemistry*, 35(4): 1265-1269.

Dermer, G.B. "Another Anniversay for the War on Cancer" (1994) *Bio/Technology*, 12: 320.

Dissanayake, S., et al. "The Wnt4A/Protein Kinase C Pathway Mediates Motility in Melanoma Cells via the Inhibition of Metastasis Suppressors and Initiation of an Epithelial to Mesenchymal Transition" (2007) *J Biol. Chem*. 282(23): 17259-17271.

European Office Action dated Oct. 26, 2011 issued in EP Application No. 06 747 832.1.

European Search Report dated Feb. 14, 2012 issued in EP Application No. 09806925.5.

European Search Report dated Oct. 7, 2011 issued in EP Application No. 11171215.4.

Feldman, B.J., et al. "The development of androgen-independent prostate cancer" (2001) *Nature*, 1:34-45.

Fernandez-Cobo, M., et al. "Expression of *Wnt5A* and *Wnt10B* in non-immortalized breat cancer cells" (2007) *Oncology Reports*, 17:903-907.

Gouon, V., et aL "UP-regulated expression of the β3 integrin and the 92-kDA gelatinase in human HT-144 melanoma cell tumors grown in nude mice", (1996) *Int. J. Cancer*, 68(5):650-662.

Gura, T. "Systems for identifying new drugs are often faulty" (1997) *Science*, 278:1041-1042.

Heinlein, C.A., et al. "Androgen receptor in prostate cancer" (2004) *Endocrine Reviews*, 25(2):276-308.

Hoek, K.S., et al. "Metalastatic potential of melanomas defined y specific gene expression profiles with no BRAF signature", *Pigment Cell Reseach*, (2006) 19(4):290-302.

Huang, C.L., et al. "Wnt5A expression is associated with the tumor proliferation and the stromal vascular endothelial growth factor—An expression in non-small-cell lung cancer" (2005) *Journal of Clinical Oncology*, 23(34):8765-8773.

Humphrey, P.A. "Gleason grading and prognostic factors in carcinoma of the prostate" (2004) *Modern Pathology*, 17:292-306.

International Preliminary Report on Patentability dated Feb. 15, 2011 issued in PCT Application No. PCT/SE2009/050935.

International Preliminary Report on Patentability dated Jan. 7, 2014 issued in PCT Application No. PCT/SE2012/050738.

International Search Report dated Nov. 18, 2009 issued in PCT Application No. PCT/SE2009/050935.

International Search Report dated Sep. 18, 2012 issued in PCT Application No. PCT/SE2012/050738.

Iozzo, R.V., et al. "Aberrant expression of the growth factor Wnt5A in human malignancy" (1995) *Cancer Research*, 55:3495-3499.

Janji, B., et al. "Autocrine TGF-β-regulated expression of adhesion receptors and integrin-linked kinase in HT-144 melanoma cells correlates with their metastatic phenotype", (1999) *Int. J. Cancer*, 83(2):255-262.

Japanese Office Action dated Oct. 31, 2011 issued in JP Application No. 2008-514590 with English translation.

Jemal, A., et al. "Cancer Statistics, 2010" (2010) *Ca Cancer Journal for Clinicians*, 60(5):277-300.

Jin, E.J., et al. "Wnt-5a is involved in TGF-β3-stimulated chondrogenic differentiation of chich wing bud mesenchymal cells", (2006) *Int. J. Biochemistry & Cell Biology*, 38(2):183-195.

Jönsson, M., et al. "Loss of Wnt-5a protein is associated with early relapse in invasive dectal breast carcinomas", (*2002*) *Cancer Research*, 62:409-416.

Jönsson, M., et al. "Repression of Wnt-5a impairs DDR1 phosphorylation and modifies adhesion and migration of mammary cells" (2001), *Journal of Cell Science*, 114: 2043-2053.

Kawano, Y., et al. "Secreted frizzled-related protein-1 is a negative regulator of androgen receptor activity in prostate cancer" (2009) *British Journal of Cancer*, 100:1165-1174.

Khaja, S., et al. "Elevated level of Wnt5a protein in localized prostate cancer tissue is associated with better outcome" (2011) *PloS ONE*, 6: e26539: 1-11.

Kremenevskaja N., et al. "Wnt-5a has tumor suppressor activity in thyroid carcinoma" (2005) *Oncogene*, 24: 2411-2154.

Kurayoshi, M., et al. "Expression of Wnt-5a is correlated with aggressiveness of gastric cancer by stimulating cell migration and invasion", (2006) *Cancer Research*, 66(21):10439-10448.

Kurayoshi, M., et al. "Post-translational palmitoylation and glycosylation of Wnt-5a are necessary for its signaling", (2007) *Biochem. J.*, 402:515-523.

Le, Y., et al. "Formyl-peptide receptors revisited", (2002) *Trends in Immunology*, 23(11):541-548.

Leandersson, K., et al. "Wnt-5a mRNA translation is suppressed by the Elav-like protein HuR in human breast epithelial cells" (2006) *Nuceic Acid Research*, 34(14):3988-3999.

Lewis, T.B., et al. "Molecular classification of melanoma using real-time quantitative reverse transcriptase-polymerase chain reaction", (2005) *Cancer*, 104(8):1678-1686.

Liang, H., et al. "Wnt-5a inhibits B cell proliferation and functions as a tumor suppressor in hematopoietic tissue", (2003) *Cancer Cell*, 4(5):349-360.

Liu, X.H., et al. "Expression of Wnt-5a and its clinicopathological significance in hepatocellular carcinoma", (2008) *Digestive and Liver Diseases*, 40(7):560-567.

Logan, C., et al. "The Wnt signaling pathway in development and disease" (2004) *Annual Review of Cell & Developmental Biology*,20:781-810.

McDonald, S.L., et al. "The opposing roles of Wnt-5a in cancer" (2009) *British Journal of Cancer*, 101:209-214.

Nusse, R., et al. A new nomenclature for int-1 and related genes: the Wnt gene family (1991) *Cell*, 64.

Office Action dated Aug. 17, 2009 issued in U.S. Appl. No. 11/946,303.

Office Action dated Jul. 17, 2012 issued in U.S. Appl. No. 13/058,036.

Office Action dated Apr. 2, 2010 issued in U.S. Appl. No. 11/946,303.

Office Action dated Aug. 22, 2013 issued in U.S. Appl. No. 11/946,303.

Office Action dated May 8, 2009 issued in U.S. Appl. No. 11/946,303.

Office Action dated May 8, 2012 issued in U.S. Appl. No. 13/058,036.

Pakala, R., et al. "Inhibition of arterial thrombosis by a peptide ligand of the thrombin receptor", (2000) *Yhtombosis Research*, 100(1):89-96.

Pierschbacher, M.D., et al. "Variants of the cell recognition site of fibronetin that retain attachment-promoting activity", (1984) *Proceedings of the National Academy of Science*, 81(19):5985-5988.

Qian, D., et al. "Wnt5a functions in planar cell polarity regulation in mice" (2007) *Developmental Biology*, 306:121-133.

(56) References Cited

OTHER PUBLICATIONS

Roarty, K., et al. "Wnt-5a is required for proper mammary gland development and TGF-β-mediated inhibition of ductal growth", (2007) *Development*, 134:3929-3939.

Rost, B., "PHD: Predicting one-dimensional protein structure by profile-based neutral networks", (2003) *Methods in Enzymology*, 266:525-539.

Rothhammer, T., et al. "Bone morphogenic proteins are overexpressed in malignant melanoma and promote cell invastion and migration", (2005) *Cancer Research*, 65:448-456.

Sen, M., et al. "Blockade of Wnt-5a/frizzled 5 signaling inhibits rheumatoid synoviocyte activation", (2001) *Arthritis and Rheumatism*, 44(4):772-781.

Slusarski, D.C., et al. "Modulation of embryonic intracellular $Ca^{2+}$ signaling by Wnt-5A" (1997) *Developmental Biology*, 182:114-120.

Säfholm, A., et al. "A formylated Hexapeptide Ligand Mimics the Ability of Wnt-5A to Impair Migration of Human Breast Epithelial Cells", (2006) *The Journal of Biological Chemistry*, 281(5), 2740-2749.

Säfholm, A., et al. "The Wnt-5a—Derived Hexapeptide Foxy-5 Inhibits Breast Cancer Metastasis in vivo by Targeting Cell Motility", (2008) *Clin Cancer Res*, 14(20): 6556-6563.

Thiele, S., et al. "Expression profile of ENT molecules in prostate cancer and its regulation by aminobisphonates" (2011) *Journal of Cellular Biochemistry*, 112:1593-1600.

Truica, C.I., et al. "β-Catenin affects androgen receptor transcriptional activity and ligand specificity" (2000) *Cancer Research*, 60:4709-4713.

Tsukamoto, A.S., et al. "Expression of the int-1 gene in transgenic mice is associated with mammary gland hyperplasia and adenocarcinomas in male and female mice" (1988) *Cell*, 55:619-625.

VanBelle, P., et al. "Melanoma -associated expression of transforming frowth factor-β isoforms", (1996) *American J. Pathology*, 148(6): 1887-1894.

Verras, M., et al. "Cross-talk between Wnt and androgen signaling pathways in the pathogenesis of prostate cancer" (2005) *Proceedings of the American Associate for Cancer Research Annual Meeting* 46: 435.

Wang, Q., et al. "A novel role for Wnt/$Ca^{2+}$ signaling in actin cytoskeleton remodeling and cell motility in prostate cancer" (2010) *Plos One*, 5(5):e10456.

Wang, Q., et al. "Hypomethylation of WNT5A, CRIP1 and S100P in prostate cancer" (2007) Oncogene, 26:6560-6565.

Weeraratna, A., et al. "Wnt5a signaling directly affects cell motility and invasion of metastatic melanoma" (2002) *Cancer Cell*, 1: 279-288.

Wegiel, B., et al. "Multiple cellular mechanisms related to cyclin Al in prostate cancer invasion and metastasis" (2008) *Journal of the National Cancer Institute*, 100:1022-1036.

Yamamoto, H., et al. "Wnt5a signaling is involved in the aggressiveness of prostate cancer and expression of metalloproteinase" (2010) *Oncogene* 29(14): 2036-2046.

Zips, et al. In vitro and in vivo evaluation of new anticancer drugs, In vivo, 19: 1-8 (2005).

* cited by examiner

A

B

TREATMENT OF PROSTATE CANCER AND A METHOD FOR DETERMINING THE PROGNOSIS FOR PROSTATE CANCER PATIENTS

PRIORITY STATEMENT

This application is a national stage application under 35 U.S.C. §371 of PCT International Application No. PCT/SE2012/050738 which has an International filing date of 28 Jun. 2012 and claims priority under 35 U.S.C. §119 to Sweden Application No. 1150619-3 filed 1 Jul. 2011. The contents of each application recited above are incorporated herein by reference in their entirety.

REFERENCE TO A SEQUENCE LISTING

This application contains references to amino acid sequences and/or nucleic acid sequences which have been submitted concurrently herewith as the sequence listing text file entitled "2044976_1.txt", file size 3 KiloBytes (KB), created on 10 Jan. 2013. The aforementioned sequence listing is hereby incorporated by reference in its entirety pursuant to 37 C.F.R. §1.52(e)(5).

FIELD OF THE INVENTION

The present invention relates to a Wnt5a protein and/or a peptide thereof possessing Wnt5a signaling properties for use in the treatment of prostate cancer in a patient. The invention further relates to a method for determining a prognosis for a patient having prostate cancer, and to a kit for performing said method.

BACKGROUND

Wnt5a is a non-canonical secreted glycoprotein of the Wnt family that plays an important role in cancer development and progression.

Peptides derived from Wnt5a, including the N-formylated hexapeptide Foxy5, have been described earlier, i.a. in WO 01/32708 and WO 2006/130082. These peptides have been shown to be agonists of Wnt5a signaling. The use of such a peptide in a mouse breast cancer model has demonstrated its ability to significantly inhibit the metastatic spread from the primary tumor inoculated and growing in a mammary fat pad. In WO 2010/019103 it has been shown that by modifying such peptides in a certain way it is possible to change the agonist function to that of an antagonist, and further that such antagonists may be used in treatment of melanoma and gastric cancer.

Previous studies report that Wnt5a is upregulated in prostate cancer and suggested that Wnt5a affects migration and invasion of prostate tumor cell.

Prostate cancer (PCa) is the leading cancer affecting men of all races and the second most leading cause of death in developed countries [1]. Androgens and the androgen receptor (AR) play critical roles not only in normal development, growth and function of the prostate gland but also in carcinogenesis and progression of PCa [2]. Initially, PCa cells are commonly AR dependent for their growth and survival, and hence respond to androgen deprivation therapy (ADT), but in later stages PCa cells become androgen-insensitive, and fatal castration-resistant prostate cancer (CRPC) develops [3]. The molecular mechanisms responsible for transition into CRPC are poorly understood, however, the most consistent change associated with castration resistant growth in global gene expression profiles of PCa xenografts was an increase in the AR mRNA levels [4]. Increased expression of AR is considered to be a key feature of CRPC and it has been demonstrated as a consequence of either mutation or amplification of AR or by increased expression caused by deregulated growth factors or various co-regulators [5]. Although we have access to prognostic factors in PCa, including Gleason grade, TNM stage, surgical margin status and serum PSA levels, there is an urgent need to identify novel biomarkers, which can significantly improve, either alone or in combination of other biomarkers, our ability to predict outcome in PCa patients. Previous studies have suggested a possible relationship between AR and Wnt-β-catenin signaling pathways during the development and progression of PCa [6,7].

Recently, attention has been drawn to the role of Wnt proteins and Wnt signaling in PCa. The name Wnt comes from "wingless-related MMTV integration site" and was originally suggested by Nusse and co-workers in 1991 [8]. Wnt proteins constitute a family of nineteen secreted glycoproteins that play important roles during development and in cell fate specification, cell migration and cell polarity [9,10]. Wnt proteins can be classified into at least two subfamilies; canonical Wnts that promote β-catenin-mediated transcription and non-canonical Wnts. Wnt signaling occur in an auto- or paracrine fashion through binding of secreted Wnt molecules to seven transmembrane Frizzled receptor proteins (Fz) in the absence or presence of co-receptors such as LRP 5/6 and ROR [10]. Several Wnt signaling components have also been implicated in genesis of human cancers; overexpression of Wnt-1 was observed in mammary epithelial adenocarcinoma [11] and in several PCa cell lines and PCa tissues. Wnt-1 expression positively correlated with Gleason score, β-catenin and with serum PSA levels [12]. In addition, based on the determination of Wnt5a mRNA levels in prostate tumors it has been suggested that abnormal expression of the non-canonical Wnt5a is involved in PCa [13].

Wnt5a, one of the most studied non-canonical Wnts, is an essential Wnt protein in inducing and controlling the Wnt/planar cell polarity (PCP) and the Wnt/$Ca_2$+ pathways [14, 15]. In addition, Wnt5a has not only been demonstrated to counteract the Wnt/β-catenin pathway but also, in specific contexts, to activate this pathway [16]. The possibility of Wnt5a to induce different downstream signaling events can at least in part explain the presence of reports suggesting an ambiguous nature of Wnt5a; having either a tumor suppressor or tumor promoting function depending on context and tumor type [16]. Previous studies have shown that Wnt5a is down-regulated in certain malignancies including colorectal cancer (protein expression) [17], neuroblastoma (mRNA levels) [18], invasive ductal breast carcinomas (protein expression) [19,20] and leukaemias (mRNA levels) [21], indicating a tumor suppressing effect of Wnt5a.

Interestingly, other reports have instead suggested an oncogenic effect of Wnt5a primarily based on an upregulation in breast cancer cells (mRNA levels) [22], gastric cancer (protein expression) [23], melanoma (protein expression) [24], lung cancer and prostate cancer (mRNA expression) [13]. Aberrant gene and protein expression of Wnt5a in PCa and possible underlying molecular mechanisms have been described in previous reports [13, 25, 26, 27]. In a recent study, based on the Affymetrix studies of normal prostate epithelial and cancer cell lines, Wang et al showed that increased transcription of the Wnt5a gene in PCa was due to hypomethylation; suggesting that epigenetic regulation of Wnt5a expression may be of importance in PCa progression [28]. Any conclusion made from data from an Affymetrix analysis without a simultaneous analysis of Wnt5a protein expression is dangerous since the Wnt5a mRNA has a long untranscribed 3'-region open for translational regulation. Data supporting such a translational regulation of Wnt5a protein expression has previously been reported [19,29].

Recent studies have shown increased Wnt5a and protein levels in PCa compared to benign tissue [25,26]. Yamamoto et al demonstrated in vitro that knockdown of Wnt5a reduced the invasive properties of DU145, and over-expression of Wnt5a stimulated invasion of PC3 cells [25]. In contrast, Wang Q and co-workers demonstrated that recombinant Wnt5a did not induce an increased motility in the same PC3 cells [26]. In addition, it has been shown by immunohistochemistry (IHC) that Wnt5a expression correlated with Gleason score≥8 in 24 patients from a cohort of 98 PCa patients that had undergone radical prostatectomy. This could indicate that Wnt5a promotes aggressiveness, since patients with low Wnt5a levels had a better relapse-free survival compared to patients with high Wnt5a levels [25].

ITEMIZED EMBODIMENTS OF THE INVENTION

Different embodiments of the invention are identified below in the following itemized listing:

Item 1. A Wnt5a protein or peptide thereof possessing Wnt5a signaling properties for use in the treatment of prostate cancer in a patient.

Item 2. A Wnt5a protein or peptide thereof possessing Wnt5a signaling properties for use according to item 1, wherein said prostate cancer is caused by cancer cells with low Wnt5a protein expression.

Item 3. A Wnt5a protein or peptide thereof possessing Wnt5a signaling properties for use according to item 1 or 2, wherein said prostate cancer is a localized prostate cancer.

Item 4. A Wnt5a protein or peptide thereof possessing Wnt5a signaling properties for use according to any one of the items 1-3, wherein said patient has undergone or will undergo radiation therapy and/or radical prosteatectomy.

Item 5. A Wnt5a protein for use according to any one of the items 1-4, wherein said Wnt5a protein is a recombinant protein.

Item 6. A Wnt5a peptide for use according to any one of the items 1-5, wherein said Wnt5a peptide is a peptide consisting of 6-20 amino acids and wherein the 6 amino acids at the C terminal end are XDGXEL (SEQ. ID. NO. 1), wherein X in position 1 is C or A and X in position 4 is M or norleucine.

Item 7. A Wnt5a peptide for use according to item 6, wherein said Wnt5a peptide is a peptide selected from the group consisting of:

MDGCEL, (SEQ. ID. NO. 2)

GMDGCEL, (SEQ. ID. NO. 3)

EGMDGCEL, (SEQ. ID. NO. 4)

SEGMDGCEL, (SEQ. ID. NO. 5)

TSEGMDGCEL, (SEQ. ID. NO. 6)

KTSEGMDGCEL, (SEQ. ID. NO. 7)

NKTSEGMDGCEL, (SEQ. ID. NO. 8)

CNKTSEGMDGCEL, (SEQ. ID. NO. 9)

LCNKTSEGMDGCEL, (SEQ. ID. NO. 10)

RLCNKTSEGMDGCEL, (SEQ. ID. NO. 11)

GRLCNKTSEGMDGCEL, (SEQ. ID. NO. 12)

QGRLCNKTSEGMDGCEL, (SEQ. ID. NO. 13)

TQGRLCNKTSEGMDGCEL, (SEQ. ID. NO. 14)

GTQGRLCNKTSEGMDGCEL, (SEQ. ID. NO. 15)
and

LGTQGRLCNKTSEGMDGCEL, (SEQ. ID. NO. 16)

or a formylated derivative of one of these peptides.

Item 8. A Wnt5a peptide for use according to item 7, wherein said Wnt5-α peptide is MDGCEL (SEQ. ID. NO. 2), or a formylated derivative thereof.

Item 9. Use of a Wnt5a protein or peptide thereof possessing Wnt5a signaling properties for the manufacture of a pharmaceutical composition for the treatment of prostate cancer in a patient.

Item 10. Use according to item 9, wherein said prostate cancer is a caused by cancer cells with low Wnt5a protein expression.

Item 11. Use according to item 9 or 10, wherein said prostate cancer is a localized prostate cancer.

Item 12. Use according to any one of the items 9-11, wherein said patient has undergone or will undergo radiation therapy and/or radical prosteatectomy.

Item 13. Use according to any one of the items 9-12, wherein said Wnt5a protein is a recombinant protein.

Item 14. Use according to any one of the items 9-13, wherein said Wnt5a peptide is a peptide consisting of 6-20 amino acids and wherein the 6 amino acids at the C terminal end are XDGXEL (SEQ. ID. NO. 1), wherein X in position 1 is C or A and X in position 4 is M or norleucine.

Item 15. Use according to item 14, wherein said Wnt5a peptide is a peptide selected from the group consisting of:

MDGCEL, (SEQ. ID. NO. 2)

GMDGCEL, (SEQ. ID. NO. 3)

EGMDGCEL, (SEQ. ID. NO. 4)

SEGMDGCEL, (SEQ. ID. NO. 5)

TSEGMDGCEL, (SEQ. ID. NO. 6)

KTSEGMDGCEL, (SEQ. ID. NO. 7)

```
                            (SEQ. ID. NO. 8)
NKTSEGMDGCEL, (SEQ. ID. NO. 9)
CNKTSEGMDGCEL, (SEQ. ID. NO. 10)
LCNKTSEGMDGCEL, (SEQ. ID. NO. 11)
RLCNKTSEGMDGCEL, (SEQ. ID. NO. 12)
GRLCNKTSEGMDGCEL, (SEQ. ID. NO. 13)
QGRLCNKTSEGMDGCEL, (SEQ. ID. NO. 14)
TQGRLCNKTSEGMDGCEL, (SEQ. ID. NO. 15)
GTQGRLCNKTSEGMDGCEL,
and (SEQ. ID. NO. 16)
LGTQGRLCNKTSEGMDGCEL,
``` or a formylated derivative of one of these peptides.

Item 16. Use according to item 15, wherein said Wnt5a peptide is MDGCEL (SEQ. ID. NO. 2), or a formylated derivative thereof.

Item 17. A method for treatment of prostate cancer wherein a therapeutically effective amount of a Wnt5a protein or peptide thereof possessing Wnt5a signaling properties is administered to a patient in need of said treatment.

Item 18. The method of item 17, wherein said prostate cancer is caused by cancer cells with low Wnt5a protein expression.

Item 19. The method of item 17 or 18, wherein said prostate cancer is a localized prostate cancer.

Item 20. The method of any one of items 17-19, wherein said patient has undergone or will undergo radiation therapy and/or radical prosteatectomy.

Item 21. The method of any one of items 17-20, wherein said Wnt5a protein is a recombinant protein.

Item 22. The method of any one of the items 17-21, wherein said Wnt5a peptide is a peptide consisting of 6-20 amino acids and wherein the 6 amino acids at the C terminal end are XDGXEL (SEQ. ID. NO. 1), wherein X in position 1 is C or A and X in position 4 is M or norleucine.

Item 23. The method of item 22, wherein said Wnt5a peptide is a peptide selected from the group consisting of:

```
                            (SEQ. ID. NO. 2)
MDGCEL, (SEQ. ID. NO. 3)
GMDGCEL, (SEQ. ID. NO. 4)
EGMDGCEL, (SEQ. ID. NO. 5)
SEGMDGCEL, (SEQ. ID. NO. 6)
TSEGMDGCEL, (SEQ. ID. NO. 7)
KTSEGMDGCEL, (SEQ. ID. NO. 8)
NKTSEGMDGCEL, (SEQ. ID. NO. 9)
CNKTSEGMDGCEL, (SEQ. ID. NO. 10)
LCNKTSEGMDGCEL, (SEQ. ID. NO. 11)
RLCNKTSEGMDGCEL, (SEQ. ID. NO. 12)
GRLCNKTSEGMDGCEL, (SEQ. ID. NO. 13)
QGRLCNKTSEGMDGCEL, (SEQ. ID. NO. 14)
TQGRLCNKTSEGMDGCEL, (SEQ. ID. NO. 15)
GTQGRLCNKTSEGMDGCEL,
and (SEQ. ID. NO. 16)
LGTQGRLCNKTSEGMDGCEL,
``` or a formylated derivative of one of these peptides.

Item 24. The method of item 23, wherein said Wnt5a peptide is MDGCEL (SEQ. ID. NO. 2), or a formylated derivative thereof.

Item 25: A method for determining a prognosis for a patient having prostate cancer, comprising the steps of:
  a) evaluating an amount of Wnt5a protein present in at least part of a sample earlier obtained from the patient and determining a sample value corresponding to the evaluated amount;
  b) comparing the sample value obtained in step a) with a reference value associated with a reference prognosis; and, if said sample value is higher than said reference value,
  c) concluding that the prognosis for said patient is better than said reference prognosis.

Item 26. A method for determining a prognosis for a patient having prostate cancer according to item 25, wherein said method comprises staining of tissue earlier obtained through a biopsy of the patient's tumor, wherein said staining is performed using standard immunohistochemical processing for Wnt5a staining, evaluation of the staining by at least one pathologist, determination of the degree of the staining as 0, 1, 2 or 3 and concluding that the prognosis for said patient is good if the degree of staining is 2 or 3.

Item 27: A kit for carrying out the method according to item 25 or 26, which comprises:
  a) a quantifiable or semi-quantifiable affinity ligand capable of selective interaction with a Wnt5a protein; and optionally
  b) reagents necessary for quantifying the amount of said quantifiable affinity ligand.

Item 28. A kit according to item 27, wherein said quantifiable or semi-quantifiable affinity ligand is selected from the group consisting of antibodies, fragments thereof and derivatives thereof.

DETAILED DESCRIPTION OF THE INVENTION

The studies leading to the present invention aimed to evaluate the prognostic value of Wnt5a protein expression in prostate cancer tissue and its potential to predict outcome after radical prostatectomy in patients with localized prostate cancer.

Conflicting reports on the role of Wnt5a in PCa progression and sparse information about Wnt5a expression in relation to clinical outcome, urged the inventors to investigate protein expression of Wnt5a in a large population-based cohort and its possible role to predict outcome after surgery for localized and predominantly low-grade PCa. This investigation was complemented with in vitro experiments to explore possible reasons for the ability of Wnt5a to act as a predictive biomarker in this patient category. In the present study the inventors confirmed that Wnt5a protein levels were upregulated in PCa compared to benign tissue but the inventors found that increased Wnt5a protein expression had a positive effect on outcome in PCa patients, as patients with high Wnt5a protein levels had a better outcome compared to patients with low Wnt5a levels after radical prostatectomy. In good agreement, the inventors also found that this ability of Wnt5a to positively affect outcome in PCa patients might be due to its ability to inhibit invasion of PCa cells in vitro.

Below it will be shown that immunohistochemical analysis of a tissue microarray containing prostate specimens of 503 patients with localized prostate cancer showed significantly higher Wnt5a protein expression in cancer compared to benign cores from the same patients (p<0.0001). Patients with high expression of Wnt5a protein had significantly better outcome in terms of time to biochemical recurrence compared to patients with low expression levels (p=0.001, 95% CI 1.361-3.570, Hazard's ratio 2.204). A combination of high Wnt5a expression with low levels of Ki-67 or androgen receptor expression had even better outcome compared to all other groups.

Furthermore, the inventors found that Wnt5a expression significantly correlated with VEGF and with Ki-67 and androgen receptor expression, although not highly significant. In vitro, the inventors demonstrated that recombinant Wnt5a decreased invasion of 22Rv1 and DU145 cells and that siRNA knockdown of endogenous Wnt5a protein led to increased invasion of 22Rv1 and LNCaP cells. Furthermore, similar to the in vitro results obtained with recombinant Wnt5a, addition of the Wnt5a derived peptide Foxy-5 significantly inhibited the invasion of 22Rv1 and DU145 prostate tumor cells (as shown in FIG. 6).

The inventors have shown that preserved overexpression of Wnt5a protein in patients with localized prostate cancer predicts a favorable outcome after surgery. This finding together with the in vitro data illustrating the ability of Wnt5a to impair the invasive properties of prostate cancer cells, demonstrates a tumor suppressing effect of Wnt5a in localized prostate cancer. These results show that Wnt5a can be used as a predictive marker. The results also show that Wnt5a protein and Wnt5a signaling peptides, i.e. peptides having essentially the same biological effect as Wnt5a protein, may be used in treatment of localized prostate cancer.

As indicated above the prostate cancer that can be treated according to the invention may be cancer caused by cancer cells with low Wnt5a protein expression. The meaning of "low" in this context is clear to the skilled person in view of the examples below. To explain this further one might add that the expression may be evaluated through immunostaining of the tissue containing the cancer cells. The immunostaining is then considered by a someone having the skills and training to make such considerations, such as a pathologist, who will score the degree of staining as 0, 1, 2 or 3 compared to an arbitrary scale. 0 indicates no staining and 1 indicates week staining. In this context 0 and 1 is considered to be the result of low expression. 2 indicates moderate staining and 3 indicates strong staining. In this context 2 and 3 are considered to be the result of high expression. When setting the score, the pathologist will consider the percentage of cells that are positive, i.e. stained, and also the intensity of the staining. The choice of the concentration of the primary antibody used for the immunostaining is selected so that the whole scale 0, 1, 2 and 3 is obtained. The antibody used in this case in any antibody that specifically binds to Wnt5a and thus enables detection of Wnt5a.

In some embodiments, the prostate cancer may be prostate cancer with a Gleason score of ≤3+4, i.e. a low to intermediate Geason score or low grade. However, in other embodiments the prostate cancer may be prostate cancer with a Gleason score of ≥4+3.

Gleason score or Gleason grade describes how closely the tumor resembles normal prostate tissue. The Gleason grading system assigns a grade to each of the two largest areas of cancer in the tissue samples. Grades range from 1 to 5, with 1 being the least aggressive and 5 the most aggressive. The two grades may be added together into a Gleason score. An added score of 2-7 (wherein 7 is constituted by 3+4 only and not 4+3) is in this context considered as low grade, while a Gleason score of 7-10 (wherein 7 is constituted by 4+3 only and not 3+4) is considered as high grade. Sometimes you see the division into 2-4 as low grade, 5-7 as intermediate grade and 8-10 as high grade, but this is not used in the present application. The Gleason score offers a good clue to your tumor's behavior: A tumor with a low Gleason score is likely to be slow-growing, while one with a high score is more likely to grow aggressively or to have already spread outside the prostate (metastasized).

In some embodiments the cancer is a localized prostate cancer.

Prior to application of the present invention, the patient may have undergone radical prostatectomy and/or radiation therapy. Alternatively, the patient might undergo radical prosteatectomy and/or radiation after application of the present invention. The invention may be used to avoid spreading of the tumor before or after radical prostatectomy and/or radiation therapy.

The Wnt5a protein or peptide thereof possessing Wnt5a signaling properties for use as above may be used for treatment of prostate cancer, such as localized prostate cancer, in a patient that has undergone or will undergo radical prostatectomy.

The Wnt5a protein used according to the invention may be a recombinant protein.

That the peptide possesses Wnt5a signaling properties means in the context of the present disclosure that the peptide has essentially the same biological function as Wnt5a protein regarding its ability to impair the migration and invasion of prostate tumor cells.

The Wnt5a peptide used according to the invention may be a peptide consisting of 6-20 amino acids and wherein the 6 amino acids at the C terminal end are XDGXEL (SEQ. ID. NO. 1), wherein X in position 1 is C or A and X in position 4 is M or norleucine.

The Wnt5a peptide used according to the invention is in some embodiments a peptide selected from the group consisting of:

```
                                        (SEQ. ID. NO. 2)
            MDGCEL, (SEQ. ID. NO. 3)
            GMDGCEL,
```

-continued

EGMDGCEL, (SEQ. ID. NO. 4)

SEGMDGCEL, (SEQ. ID. NO. 5)

TSEGMDGCEL, (SEQ. ID. NO. 6)

KTSEGMDGCEL, (SEQ. ID. NO. 7)

NKTSEGMDGCEL, (SEQ. ID. NO. 8)

CNKTSEGMDGCEL, (SEQ. ID. NO. 9)

LCNKTSEGMDGCEL, (SEQ. ID. NO. 10)

RLCNKTSEGMDGCEL, (SEQ. ID. NO. 11)

GRLCNKTSEGMDGCEL, (SEQ. ID. NO. 12)

QGRLCNKTSEGMDGCEL, (SEQ. ID. NO. 13)

TQGRLCNKTSEGMDGCEL, (SEQ. ID. NO. 14)

GTQGRLCNKTSEGMDGCEL, and (SEQ. ID. NO. 15)

LGTQGRLCNKTSEGMDGCEL, (SEQ. ID. NO. 16)

or a formylated derivative of one of these peptides. Such peptides are described in more detail in WO 01/32708 and WO 2006/130082.

In some embodiments, the Wnt5a peptide used according to the invention is MDGCEL (SEQ. ID. NO. 2).

In some embodiments, the Wnt5a peptide used according to the invention is a formylated derivative of MDGCEL (SEQ. ID. NO. 2), i.e. the N-formylated hexapeptide Foxy5.

The term "therapeutically effective amount", as used herein, relates to an amount that will lead to the desired therapeutical effect.

Another aspect of the present invention relates to a method for determining a prognosis for a patient having prostate cancer, comprising the steps of:

a) evaluating an amount of Wnt5a protein present in at least part of a sample earlier obtained from the patient and determining a sample value corresponding to the evaluated amount;

b) comparing the sample value obtained in step a) with a reference value associated with a reference prognosis; and, if said sample value is higher than said reference value, c) concluding that the prognosis for said patient is better than said reference prognosis.

As further mentioned above, the invention also relates to a kit for carrying out for determining a prognosis, wherein the kit comprises:

a) a quantifiable or semi-quantifiable affinity ligand capable of selective interaction with a Wnt5a protein; and b) reagents necessary for quantifying the amount of said quantifiable affinity ligand.

The quantifiable or semi-quantifiable affinity ligand capable of selective interaction with a Wnt5a protein may be an antibody or a fragment or a derivative of such an antibody.

Guided by the present disclosure, the person skilled in the art may select relevant reference values without undue burden. At least one example of how the reference value may be selected is illustrated in the examples below. Furthermore, the relation between sample values and survival data in a relevant group of cancer patients may be examined in line with what is described in the examples below.

A physician may use the prediction method according to the invention to obtain additional information regarding the prognosis of a prostate cancer patient, which in turn may help him or her to make informed decisions regarding following actions. In general, when deciding on a suitable treatment strategy for a patient having prostate cancer, the physician responsible for the treatment may take several parameters into account, such as the result of an immunohistochemical evaluation, the results of a PSA blood test, patient age, tumor type, stage, such as T stage of the primary tumor, grade according to Gleason scalegeneral condition and medical history. To be guided in the decision, the physician may perform a Wnt5a protein test, or order a Wnt5a protein test performed, according to the first aspect. Further, the physician may assign to someone else, such as a lab worker, to perform step a), and optionally step b), while performing step c), and optionally b), himself.

Since the prognoses for patients showing high immunological staining of Wnt5a relative to benign epithelium are generally better than those for patients showing low Wnt5a protein levels, as shown below, the physician may choose or refrain from a certain treatment regime.

In the context of the present disclosure, "establishing a prognosis" refers to establishing a specific prognosis or a prognosis interval.

In the context of the present disclosure, "prognosis" refers to the prediction of the course or outcome of a disease and its treatment. For example, prognosis may also refer to a determination of chance of survival or recovery from a disease, as well as to a prediction of the expected survival time of a patient. A prognosis may specifically involve establishing the likelihood for survival of a patient during a period of time into the future, such as three years, five years, ten years or any other period of time. A prognosis may also involve establishing the likelihood for prostate cancer relapse. A prognosis may further be represented by a single value or a range of values.

Further, in the context of the methods of the present disclosure, "earlier obtained" refers to obtained before the method is performed. Consequently, if a sample earlier obtained from a patient is used in a method, the method does not involve obtaining the sample from the patient, i.e., the sample was previously obtained from the patient in a step separate from the method.

The prognostic method of the present invention may unless otherwise stated be carried out entirely in vitro.

The term "patient", as it is used herein, relates to any human or non-human mammal male in need of treatment according to the invention. More precisely, in the context of the present disclosure, "a patient having prostate cancer" refers to a male mammal, such as a human, having a primary prostate tumor or a male mammal, such as a human, which has had a primary prostate tumor removed, wherein the removal of the tumor refers to eradicating the tumor by any appropriate type of surgery or therapy. In some embodiments, removal of surgery is the preferred option. In the method and use aspects of the present disclosure, "a patient having prostate cancer" also includes the cases wherein the patient is suspected of having prostate cancer at the time of the use or the performance of the method and the prostate cancer diagnosis is established later.

Further, in the context of the present disclosure, the "reference value" refers to a predetermined value found to be relevant for making decisions or drawing conclusions regarding the prognosis or a suitable treatment strategy for the patient.

Also, in the context of the present disclosure, a reference value being "associated" with a reference prognosis refers to the reference value being assigned a corresponding reference prognosis, based on empirical data and/or clinically relevant assumptions. For example, the reference value may be the average Wnt5a protein value in a relevant group of patients and the reference prognosis may be an average survival in the same group. Further, the reference value does not have to be assigned to a reference prognosis directly derived from prognosis data of a group of patients exhibiting the reference value.

Numerous ways of obtaining a sample value corresponding to a level of Wnt5a protein in a sample from a patient are known to the skilled person.

The sample is normally tissue from a biopsy. Alternatively, cells otherwise obtained from prostate may be used.

Step a) of the method of the above aspects involve evaluating an amount of Wnt5a protein present in at least part of the sample, and determining a sample value corresponding to the amount. The "at least part of the sample" refers to a relevant part or relevant parts of the sample for establishing the prognosis or drawing conclusions regarding suitable treatments. The person skilled in the art understands which part or parts that are relevant under the circumstances present when performing the method. For example, if evaluating a sample comprising cells, the skilled person may only consider the tumor cells, or only the nuclei of tumor cells, of the sample.

Further, in step a) an amount is evaluated and a sample value corresponding to the amount is determined. Consequently, an exact measurement of the amount of Wnt5a protein is not required for obtaining the sample value. For example, the amount of Wnt5a protein may be evaluated by visual inspection of a prepared and stained tissue sample and the sample value may then be categorized as for example high or low based on the evaluated amount.

The evaluation and determination of step a) requires some kind of processing or manipulation of the sample. It is not possible to determine the sample value by mere inspection of the sample as such. Various techniques, of which some are presented below, for such evaluation and determination, are well known to the skilled person. The methods of the present disclosure are therefore not limited to any specific technique or techniques for the performance of step a).

In some embodiments of the present disclosure, the prognosis may be a probability of survival. The survival of the present disclosure may for example be overall survival or disease free survival. Further, the "survival" may be measured over different periods, such as five, ten or 15 years. Accordingly, the survival may be a five-year, ten-year or 15-year survival. Where a reference prognosis is employed, it is of the same type as the prognosis of the patient.

In the context of the present disclosure, the terms "sample value" and "reference value" are to be interpreted broadly. The quantification of Wnt5a protein to obtain these values may be done via automatic means, via a scoring system based on visual or microscopic inspection of samples, or via combinations thereof. However, it is also possible for a skilled person, such as a person skilled in the art of histopathology, to determine the sample and reference values by inspection, e.g., of tissue slides that have been prepared and stained for Wnt5a protein expression. Determining that the sample value is higher than the reference value may thus correspond to determining, upon visual or microscopic inspection, that a sample tissue slide is more densely stained and/or exhibit a larger fraction of stained cells than a reference tissue slide. The sample value may also be compared to a reference value given by a literal reference, such as a reference value described in wording or by a reference picture. Consequently, the sample and/or reference values may in some cases be mental values that the skilled person determines upon inspection and comparison.

A reference value, found to be relevant for establishing prognosis or making treatment decisions regarding prostate cancer patients, for use as comparison with the sample value from the patient, may be provided in various ways. In view of the teachings of the present disclosure, the skilled person can, without undue burden, provide relevant reference values for performing the methods of the present disclosure.

The person performing the prognostic method of the invention may, for example, adapt the reference value to desired information. For example, the reference value may be adapted to yield the most significant prognostic information, which corresponds to the largest difference in survival between the first and the second group of the first aspect. Alternatively, the reference value may be selected such that a group of pateints having particularly good prognoses or particularly poor prognoses is singled out.

In some embodiments of the prognostic method of the invention, the reference value may correspond to the amount of Wnt5a protein expression in a healthy tissue from the patient of the method. As another example, the reference value may be provided by the amount of Wnt5a protein expression measured in a standard sample of normal tissue from another, comparable patient. As another example, the reference value may be provided by the amount of Wnt5a protein expression measured in a reference sample comprising tumor cells. The amount of protein expression of the reference sample may preferably be previously established. Consequently, the reference value may be provided by the amount of Wnt5a protein measured in a reference sample comprising cells expressing a predetermined amount of Wnt5a protein.

Consequently, in embodiments of the methods of the present disclosure, the reference value may be a predetermined value corresponding to the amount of Wnt5a protein expression in a reference sample.

Cell lines expressing a controlled amount of Wnt5a protein may be used as the reference.

One or more pictures may also be provided as the "reference sample". For example, such a picture may show an example of a tumor tissue slide stained with a certain antibody during certain conditions and exhibiting a certain nuclear intensity and/or fraction. The above discussion about the "reference sample" applies mutatis mutandis to pictures.

The cell lines or pictures may also form part of the kit according to the present invention.

In some embodiments of the invention the prognostic method may be performed in the following way. Tissue earlier obtained through a biopsy of the patient's tumor is stained using standard immunohistochemical processing for Wnt5a staining. The staining is then evaluated by at least one person having the skills and training to make such evaluation, such as a pathologist and preferably by at least one experienced pathologist. The pathologist then reviews the degree of the immunostaining and scores the degree of staining as 0, 1, 2 or 3. When deciding the degree of staining, the pathologist will consider the percentage of cancer cells that are positive, i.e. stained, and also the intensity of the staining. The patient's prognosis may be considered as good if the cancers cells are found to have high Wnt5a protein expression, i.e. a score of 2 or 3, and worse if the cancers cells are found to have low Wnt5a protein expression, i.e. a score of 0 and 1.

In this above case, step a) of the prognostic method thus includes evaluation of the amount of Wnt5a protein present in the sample by immunostaining of the sample followed by determination of the intensity of the staining. The value given to the intensity of staining of the sample thus constitutes the sample value. The reference value of step b) would then be 0 or 1, for which the reference prognosis is less favorable.

The result of the Wnt5a staining as described above may also be evaluated in combination with evaluation of analyses of the tumor cells' expression of at least one other protein, such as androgen receptor (AR), Ki-67 and/or vascular endothelial growth factor (VEGF).

The expression of these proteins is evaluated in the same way as the expression of Wnt5a. Tissue earlier obtained through a biopsy of the patient's tumor is thus stained using standard immunohistochemical processing for AR, Ki-67 or VEGF, respectively. The staining is then evaluated by at least one pathologist, preferably by at least one experienced pathologist. The pathologist then reviews the intensity of the immunostaining and scores the degree of staining as 0, 1, 2 or 3, where 0 and 1 is low and 2 and 3 are high. A low expression of AR, Ki-67 and/or VEGF in combination with a high expression of Wnt5a protein is indicative of a good prognosis, and the combinations of high expression of Wnt5a protein+ low expression of AR, high expression of Wnt5a protein+low expression of Ki-67 and/or high expression of Wnt5a protein+low expression of VEGF constitute better bases for a good prognosis for the patient compare to high expression of Wnt5a protein alone.

As mentioned above, the result of the protein staining analyses may be used in combination with other prostate cancer indicators, such as clinical and pathological tumor stage, Gleason score and the result of PSA blood tests to give a full view of the patient's condition before establishing a final prognosis.

A patient found to have a bad prognosis by the prognostic methods described above may be a patient in particular need of treatment according to the invention. Such a patient may benefit particularly by treatment with a Wnt5a protein or with a Wnt5a peptide according to the invention.

BRIEF DESCRIPTION OF THE DRAWINGS

In the examples below reference is made to the appended drawings on which.

EXAMPLES

Materials and Methods

Patients and Tissue Microarray (TMA) Construct

Figure 1:
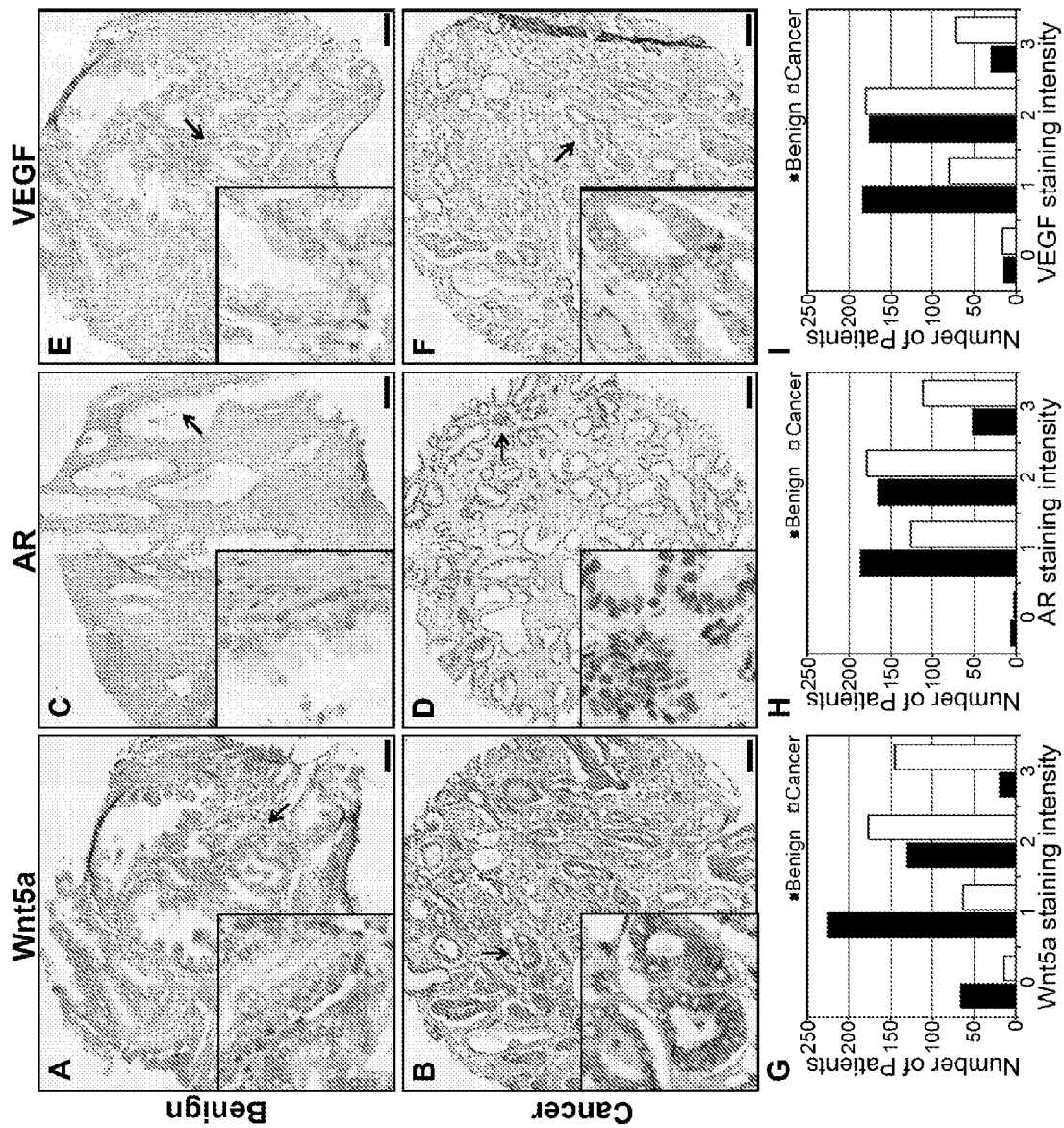
FIG. 1: shows immunohistochemical expression of Wnt5a, AR and VEGF in tissue microarray cores of primary tumors and benign specimens obtained after radical prostatectomy. A & B) The panels show representative Wnt5a immunostainings in benign and cancer tissue areas from the same patient. C & D) The panels show representative nuclear AR immunostainings in benign and cancer tissue areas. E & F) The panels outline VEGF immunostaining in benign and cancer tissue areas from the same patient. All inserts in the panels depict magnification (40×) images of the area indicated by the arrow in the larger image seen at 15× magnification. G, H & I) The panels outline graphical illustrations of Wnt5a, AR and VEGF protein expressions in benign and cancer samples in PCa patients. The bar in each panel outlines 100 μm.

A TMA was constructed from a population-based cohort of 503 PCa patients who underwent radical prostatectomy between 1988 and 2003 at the Department of Urology, Skåne University Hospital, Malmö, Sweden as previously described [36]. From each patient, benign and malignant cores in duplicate were mounted in a total of 17 paraffin blocks. Consecutive sections were used for IHC. A senior National Board certified pathologist examined hematoxylin and eosin stained tissues for Gleason grade and for the presence of prostatic intraepithelial neoplasia. The clinical and pathological characteristics of the PCa patients were obtained from reading the patient charts in detail and are shown in Table 1. The mean follow-up time was 41.6 months (range 1.51-205.90). BCR was defined as a blood PSA level of at least 0.2 ng/ml with a subsequent confirmatory value.

Source of Antibodies

The following antibodies were used for immunostainings: Wnt5a (rabbit polyclonal): antibody was developed in the inventors' laboratory against a Wnt5a sequence with 100% homology between human and mouse [20]; androgen receptor (AR) (code AR 441, mouse monoclonal, Thermo Fisher Scientific Inc., Freemont, Calif.), Ki-67 (mouse monoclonal, MIB-1 code M7240, Dako Denmark A/S, Glostrup, Denmark); VEGF A-20 (rabbit polyclonal, code sc-152, Santa Cruz Biotechnology, Inc., Santa Cruz, Calif.); β-actin (mouse monoclonal, code C4, MP Biomedicals, Solon, Ohio), α Tubulin (mouse monoclonal, sc-32293, Santa Cruz Biotechnology).

Immunohistochemistry (IHC)

Consecutive sections of 4 μm thickness were mounted on Superfrost Plus (Menzel Glaser, Braunschweig, Germany) glass slides and de-paraffinized with xylene and rehydrated in decreasing concentrations of ethanol solutions. For antigen retrieval TMA slides were heated in PT Link (Dako) from 65° C. to 98° C. for 40 min and then processed for immunohistochemical staining for Wnt5a (final dilution 1:100), AR (1:100), Ki67 (1:100) and VEGF (1:100) using EnVision™ 382 Flex, High pH reagent (code K8010, Dako) in Autostainer Plus according to the manufacturer's protocol (Dako). Immunostaining of Wnt5a, Ki-67, AR and VEGF were scored independently by pathologists LH, AE and RE. Overall, scoring pattern matched in nearly 80% of cases in staining intensities as well as percentage of positive cells. Remaining 20% cases where there was a disagreement over scoring were re-examined together and were scored after coming to a conclusion. In general, the cores were scored 0 (no staining), 1 (weak staining), 2 (moderate staining) or 3 (strong staining) based on the staining intensities and/or percentage of positive cells. Wnt5a and VEGF slides were scored based on the cytoplasmic staining whereas nuclear staining was evaluated for AR staining. Ki-67 slides were scored as 0 (0-1%), 1 (1-3%), 2 (4-10%) and 3 (11-20%) based on nuclear fraction positivity. While performing statistics protein expression scores were separated into two groups based on their staining intensities; scores 0 & 1 are grouped as weak/low and strong/high group contains scores of 2 & 3.

For IHC studies and correlation analyses on Wnt5a, Ki-67, AR and VEGF, patients with no Gleason score information available (29), and patients who received hormonal and/or radiation therapy (39) were excluded, leaving 464 patients for analyses. During TMA construction some cores were either lost, or were not properly placed on slides, or were 398 damaged and were not available to score; hence immunostaining data of proteins contains missing values (Table 2).

Cell Lines

Four human PCa cell lines LNCaP, 22Rv1, PC-3, and DU145 were purchased from American Type Culture Collection [ATCC] (Manassas, Va.). The immortalized PNT2 normal human prostate epithelial cells (cat No. 95012613) were obtained from European Collection of Cell Cultures (ECACC), (Sigma-Aldrich, St. Louis, Mo.). LNCaP, 22Rv1, DU145 and PNT2 cells lines were cultured in RPMI-1640 medium, supplemented with 10% fetal bovine serum (FBS) and 1% pest (penicillin and streptomycin). PC-3 cells were grown in Hyclone Ham's F12 medium supplemented with 10% FBS and 1% pest. All in vitro experiments were performed when cells were ~70% confluent. For invasion assay experiments cells were grown in serum free medium (SFM) for 24 hours. RPMI-1640 medium (R0883), FBS (F6178), penicillin streptomycin (P0781) were purchased from Sigma-Aldrich, whereas Ham's F12 medium (SH30026.01) was obtained from Thermo-Scientific (Waltham, Mass.). All cell lines were regularly tested for the absence of mycoplasma infection.

Western Blot Analysis

Protein expression was examined by western blot analysis. In brief, cells were washed with PBS, trypsinized (in trypsin for 3 min), centrifuged at 1000 rpm for 4 minutes. Cells were lysed on ice in RIPA buffer (50 mM Tris-HCl pH 7.4, 150 mM NaCl, 1% Triton x-100, 1% sodium deoxycholate, 0.1% sodium dodecyl sulfate, 1 mM EDTA, 0.1 mg/mL Phenylmethylsulphonyl fluoride with the addition of Complete Mini protease inhibitor cocktail (Roche, Mannheim, Germany) for 30 min, centrifuged at 15,000 rpm for 25 min at +4° C., and protein lysates were collected as supernatants. After measuring protein concentration by Bradford assay, 100 μg of each protein sample was loaded on 10% SDS-polyacrylamide gels. Proteins were separated using gel electrophoresis and transferred to Hybond ECL nitrocellulose membranes (Amersham Pharmacia Biotech, Buckinghamshire, UK). For blocking of non-specific binding, nitrocellulose membrane was blocked in 5% dry milk for 45 min at room temperature, washed twice in buffer (0.05% Tween in PBS) for 10 min, and then incubated overnight separately with rabbit polyclonal Wnt5a antibody (1:750 in 2.5% dry milk) or mouse monoclonal AR (1:500 in 2.5% dry milk) at +4° C. After incubation (for 60 min at room temperature) 429 with horseradish peroxidase-conjugated anti-rabbit secondary antibody (Amersham Life Science, Alesbury, UK) (1:10000 in 5% dry milk)

for Wnt5a and horseradish peroxidase-conjugated goat anti-mouse secondary antibody (Dako) (1:10000 in 5% dry milk) for AR and washing away the unbound antibodies, membrane-bound antibody was detected by using Western blotting Luminol Reagent (Santa Cruz). Membranes were then stripped using stripping solution (Restore PLUS Western Blot Stripping Buffer, Thermo Scientific) and reprobed for β-actin (1:3,000 in 2.5% dry milk) or α Tubulin (1:1000 in 2.5% dry milk).

Transfection with Wnt5a siRNA

Two different Silencer® Select Pre-designed (Inventoried) Wnt5a siRNAs (S1 and S2) and Silencer® Select negative control siRNA were purchased from Applied Biosystems (Ambion, Calif.). A cocktail of two different siRNAs (120 nM) in nuclease-free water was transfected into $1\times10^5$ cells in a total volume 250 μL of serum free medium using 10 μL of Lipofectamine 2000 (Invitrogen, Carlsbad, Calif.). Media was changed after 5 hours of transfection. After 24 hours of transfection, media was changed to SFM, and cells were used 24 hours later for analysis of their Wnt5a protein expression and invasive capacities.

Invasion Assay

Cell invasion capacities were measured in a standard commercial invasion assay. In this study the inventors used BD BioCoat™ Matrigel™ Invasion Chambers (BD Biosciences, Bedford, Mass.) in accordance with the manufacturer's protocol. Briefly, cells were grown in SFM for 24 h, harvested using versene (Invitrogen, Carlsbad, Calif.), washed in PBS and resuspended at a concentration of 50,000 cells/ml in SFM. To the lower well 0.7 ml serum containing medium (10% FBS) was added. To the invasion chamber 0.5 ml (25,000 cells) of the cell suspension, containing either 0.4 μg/ml recombinant Wnt5a (rWnt5a, R&D Systems, Minneapolis, Minn.) or PBS (with 0.2% BSA) was added, and were incubated for 24 h at 37° C. After 24 h cells that invaded through the Matrigel were fixed in 4% paraformaldehyde and stained with 0.2% crystal violet in 20% methanol (Sigma-Aldrich, Saint Louis, Mo., USA). Remains of the Matrigel were removed with a cotton stick moistened in PBS. Membranes from invasion chambers were separated and mounted on glass slide using VectaShield® mounting medium with DAPI (Vector Laboratories, Burlingame, Calif.). Invaded cells were counted either in an 460 inverted microscope or in Olympus BX51 Fluorescence Microscope (Olympus optical Co. Ltd, Japan).

Statistical Analysis

All statistical analyses were performed using SPSS version 17.0 (SPSS, Chicago, Ill.) and Microsoft Excel 2010. Since patients' samples were present in duplicates, the best score of the two cores (if available) was used for statistical analyses. Patients receiving preoperative hormonal treatment or radiation therapy (n=39), patients with no information available on Gleason score (29) and the patients where PSA levels were not completely 0 after radical prostatectomy and hence no BCR (n=75) were excluded, leaving a total of 397 patients for survival and multivariate statistical analyses. For statistical analyses patient material was divided into two groups based on Gleason scoring; patients with Gleason score 5 to 7 (with 3+4 cases only) were grouped as "low-grade cancers", and patients with Gleason score 7 (4+3 cases only) to 10 were put together as "high-grade cancer" group. Wilcoxon Signed Ranks test was used to examine any significant difference in Wnt5a protein expression between cancer and benign tissues. Spearman's rank-order correlation was performed to know significant correlations between Wnt5a, AR, Ki-67 and VEGF staining. Kaplan-Meier method was used to determine BCR-free survival (outcome) and Log Rank (Mantel-Cox) test was used to compare BCR free survival among different Wnt5a expression groups. For survival analysis staining intensities of different proteins were grouped into two; no/weak staining in group "1" (low) and moderate/strong staining in group "2" (high). In some analyses, expression pattern of two different proteins were grouped together, for example, while performing survival curves and Cox regressional analyses Wnt5a and AR staining intensities were grouped together, making four different groups. Patients with low Wnt5a and low AR staining constituted group 1, group 2 had patients with low Wnt5a and high AR staining, patients with high Wnt5a and low AR were kept in group 3, whereas group 4 consisted of patients with high Wnt5a and high AR staining intensities. The same criterion was applied while combining Wnt5a staining intensities with Ki-67/VEGF scorings.

Results

Immunohistochemical Evaluation of Wnt5a, AR, Ki-67 and VEGF

A tissue microarray (TMA) construct with duplicate cores of both benign and malignant tissues from 503 patients (patients' characteristics in Table 1) that had undergone radical prostatectomy, was immunostained for Wnt5a, AR, Ki-67 and VEGF (FIG. 1 A-F). Wnt5a protein expression was detected in the cytoplasmic compartment of epithelial cells and occasionally in stromal cells of both cancer and benign tissue specimens. Cancer tissues from most patients (82%) showed a homogenous strong cytoplasmic immunostaining, whereas a majority of benign tissues (65%) showed weak immunoreaction supporting that an up-regulation of Wnt5a protein occurs in cancer tissue. Results from manual scoring of cytoplasmic staining intensities in malignant and benign epithelial cells are illustrated in FIG. 1 G-I. The difference between Wnt5a staining intensities in cancer and benign samples was found to be significant (p<0.0001) when paired Wilcoxon rank sum test was performed. In nearly 80% of the patients the inventors found strong Wnt5a staining intensity (arbitrary unit 2 or 3) in cancer cores, whereas only 35% patients displayed strong staining in benign tissue samples. Further details on the scoring data from Wnt5a, AR, Ki-67 and VEGF stained cores are given in Table 2.

TABLE 1

Summary of patient characteristics 643 (n = 503)

| Characteristic | Median (IQR) or Frequency (%) |
|---|---|
| Age at diagnosis (years) | 63.13 (59.33, 66.18) |
| Preoperative PSA (ng/ml) | 7.2 (5.03, 11.07) |
| Clinical Stage | |
| T1 | 181 |
| T2 | 233 |
| T3 | 9 |
| Pathological Gleason Score | |
| ≤3 + 4 | 423 (84.1%) |
| ≥4 + 3 | 51 (10.1%) |
| Extracapsular extension | 250 (49.7%) |
| Seminal vesicle invasion | 55 (10.9%) |
| Positive surgical margins | 259 (51.5%) |
| Lymph node involvement (LNI) * | 3 (2%) |

Abbreviation: IQR, Interquartile range
* Information about LNI was available only for 153 patients

TABLE 2

Scoring data from Wnt5a, AR, VEGF and Ki-67 immunostained cores from benign and cancer tissues in duplicates mounted in a TMA

| Score | Wnt5a Benign | Wnt5a Cancer | AR Benign | AR Cancer | VEGF Benign | VEGF Cancer | Ki-67 Benign | Ki-67 Cancer |
|---|---|---|---|---|---|---|---|---|
| 0 | 60 (15) | 14 (4) | 6 (1.5) | 2 (0.5) | 14 (3) | 16 (5) | 55 (14.2) | 21 (5.3) |
| 1 | 205 (50) | 53 (14) | 186 (45.6) | 126 (30.1) | 184 (46) | 80 (23) | 323 (83.2) | 341 (85.5) |
| 2 | 123 (30) | 162 (44) | 165 (40.4) | 179 (42.7) | 175 (44) | 180 (52) | 9 (2.3) | 33 (8.3) |
| 3 | 19 (5) | 141 (38) | 51 (12.5) | 112 (26.7) | 29 (7) | 72 (21) | 1 (0.2) | 4 (1) |
| Total | 407 (100) | 370 (100) | 408 (100) | 419 (100) | 402 (100) | 348 (100) | 388 (100) | 431 (100) |
| Missing | 57 | 94 | 56 | 45 | 62 | 116 | 76 | 65 |
| Total | 464 | 464 | 464 | 464 | 464 | 464 | 464 | 464 |
| p-value | | <0.0001 | | <0.0001 | | <0.0001 | | <0.0001 |

Scoring is based on arbitrary units with 0 representing no staining, 1 as weak staining, 2 as moderate staining and 3 as strong staining. For Ki-67 the percentage of nuclear positivity was scored as 0 (0-1% positive nuclei), 1 (1-3% positive nuclei), 2 (4-10% positive nuclei) and 3 (11-20% positive nuclei). The p values at the bottom row of the table indicate statistically significant differences between benign and cancer samples from same patient when Wilcoxon rank sum tests were performed. The values in the brackets represent number of patients (%) based on the highest score from each individual duplicate. Patients who underwent radiation therapy and/or hormonal therapy before radical prostatectomy were excluded from the IHC analysis.

Androgen receptor staining was predominantly nuclear as expected and in general more intense in cancer compared to benign tissue specimens as detailed in Table 2. Seventy percent of tumor cores were intensely stained compared to 53% of benign cores.

Figure 4:
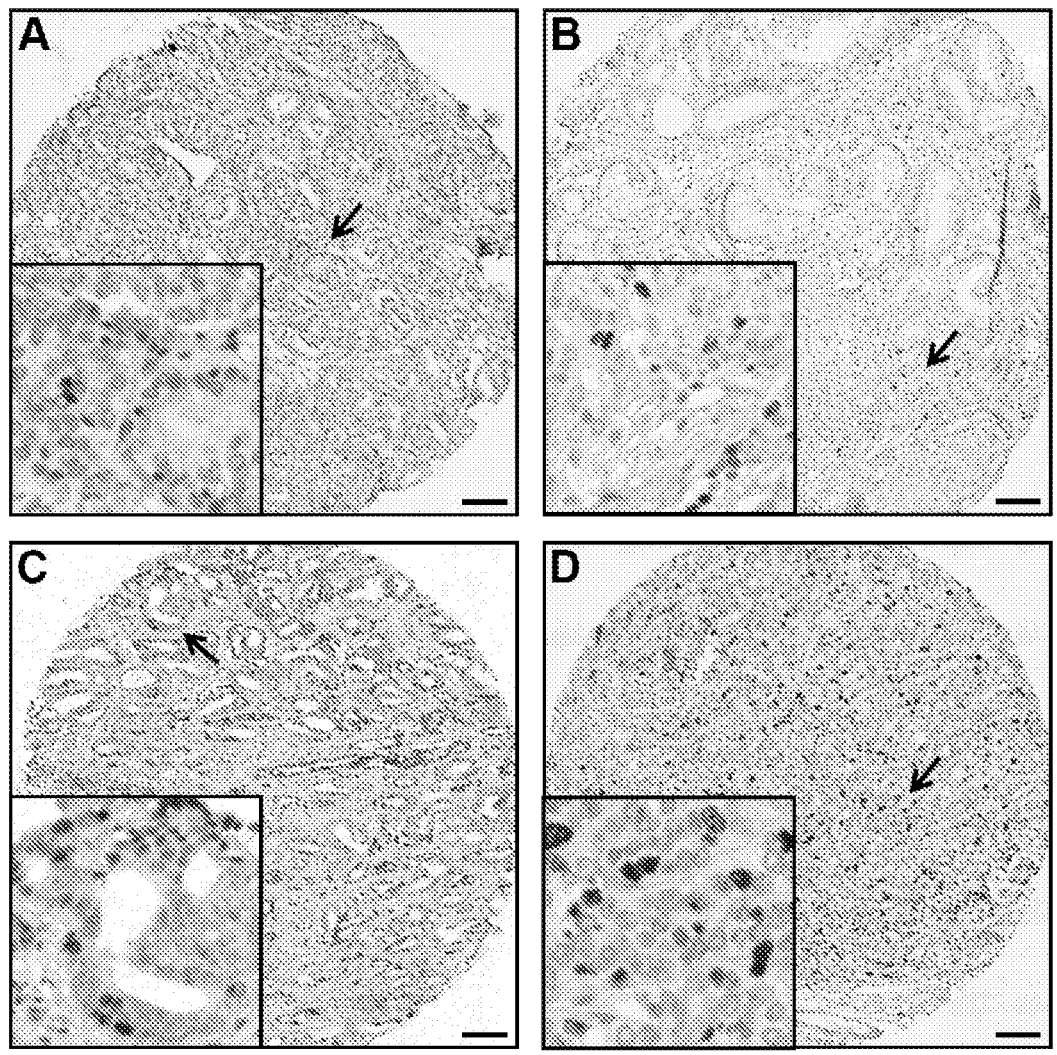
FIG. 4: Representatives of Ki-67 nuclear fraction immunostainings. A) The panel represents cancer core with no Ki-67 nuclear staining. B) The panel represents cancer core with 1-3% Ki-67 nuclear staining, C) The panel shows cancer core with 4-10% of nuclei stained positive for Ki-67 D) The panel shows cancer core with more than 10% of nuclei stained positive for Ki-67. All inserts in the panels depict magnification (40×) images of the area indicated by the arrow in the larger image seen at 15× magnification. The bar in each panel outlines 100 μm.

Nuclear Ki-67 expression was used as a proliferation marker (see FIG. 4). There were significant differences in Ki-67 staining between cancer and benign cores, as 14% of the benign cores were negative for Ki-67, whereas only 5% of the cancers cores were Ki-67 negative. Regarding positive Ki-67 nuclear staining, nearly 9% of the cancer cores had a staining score more than 2, whereas the corresponding number for the benign cores was only 2.5% (Table 2).

VEGF expression, as a surrogate marker for angiogenesis, was observed in the cytoplasm of both malignant and benign epithelial cells, with cancer areas showing higher staining compared to benign. More than 73% of the cancer cores showed strong VEGF immunostaining, whereas only 51% of the benign cores showed strong immunoreaction (Table 2).

The difference between AR, Ki-67 and VEGF staining intensities in cancer versus benign cores was statistically significant ($p<0.0001$) when Wilcoxon rank sum test was performed (Table 2).

Correlation of Wnt5a Tissue Expression with AR, Ki-67 and VEGF

In the present cohort Wnt5a expression showed a positive and statistically significant correlation with VEGF expression (Spearman's rho ($\rho$)=0.396, $p<0.0001$), weak but still statistically significant correlations with AR expression ($\rho$=0.159, $p$=0.007) and Ki-67 expression ($\rho$=177 0.233, $p<0.0001$) (Table 3). Most of the patients (220/365, 60%) with strong Wnt5a immunostaining in cancer tissues also exhibited intense AR staining (Table 4). A similar trend was observed when Wnt5a and VEGF were compared; 65% (219/339) of the cancer cores exhibited strong staining for both Wnt5a and VEGF. The inventors found no differences in Wnt5a immunostaining intensity when the inventors compared groups of patients with different Gleason scores. Among patients with pathological Gleason score up to 3+4 ("low grade"), 81% had elevated Wnt5a protein expression compared to 86% of the patients with higher Gleason score (data not shown). Similarly, no correlation was observed between Wnt5a staining and pathological T stage, clinical T stage, surgical margin status or seminal vesicle invasion (data not shown).

TABLE 3

Spearman's correlation coefficients ($\rho$) when Wnt5a protein expression 706 was analyzed for possible correlation with other tissue biomarkers in the cancer cores from 464 PCa patients

| | | Ki-67 | AR | VEGF |
|---|---|---|---|---|
| Wnt5a | $\rho$ | 0.212** | 0.142** | 0.395** |
| | p-value | <0.0001 | 0.007 | <0.0001 |

**Correlation is significant at the 0.01 level (2-tailed).

TABLE 4

Multivariate analysis of factors influencing biochemical relapse-free survival

| Factors | Groups | n (%) | Hazard ratio (95% CI) | $\chi^2$ | p - value |
|---|---|---|---|---|---|
| Wnt5a Staining | High | 321 (80.7) | 1 (Reference) | 10.863 | 0.001 |
| | Low | 77 (19.3) | 2.204 (1.361-3.570) | | |
| Wnt5a & Ki67 staining | Wnt5a high Ki67 low | 255 (73.1) | 1 (Reference) | 36.638 | |
| | Wnt5a low Ki67 low | 59 (16.9) | 2.335 (1.344-4.054) | | 0.003 |
| | Wnt5a low Ki67 high | 3 (0.6) | 14.501 (4.412-47.658) | | <0.0001 |
| | Wnt5a high Ki67 high | 32 (9.2) | 2.215 (1.128-4.351) | | 0.021 |
| Wnt5a & AR staining | Wnt5a high AR low | 81 (22.2) | 1 (Reference) | 19.769 | |
| | Wnt5a low AR low | 28 (7.7) | 3.044 (1.067-8.685) | | 0.037 |
| | Wnt5a low AR high | 36 (9.9) | 6.060 (2.489-14.756) | | <0.0001 |
| | Wnt5a high AR high | 220 (60.3) | 2.503 (1.129-5.546) | | 0.024 |
| Wnt5a & VEGF staining | Wnt5a high VEGF low | 63 (18.6) | 1 (Reference) | 13.955 | |
| | Wnt5a low VEGF low | 29 (8.6) | 2.843 (1.121-7.211) | | 0.028 |

TABLE 4-continued

Multivariate analysis of factors influencing biochemical relapse-free survival

Figure 5:
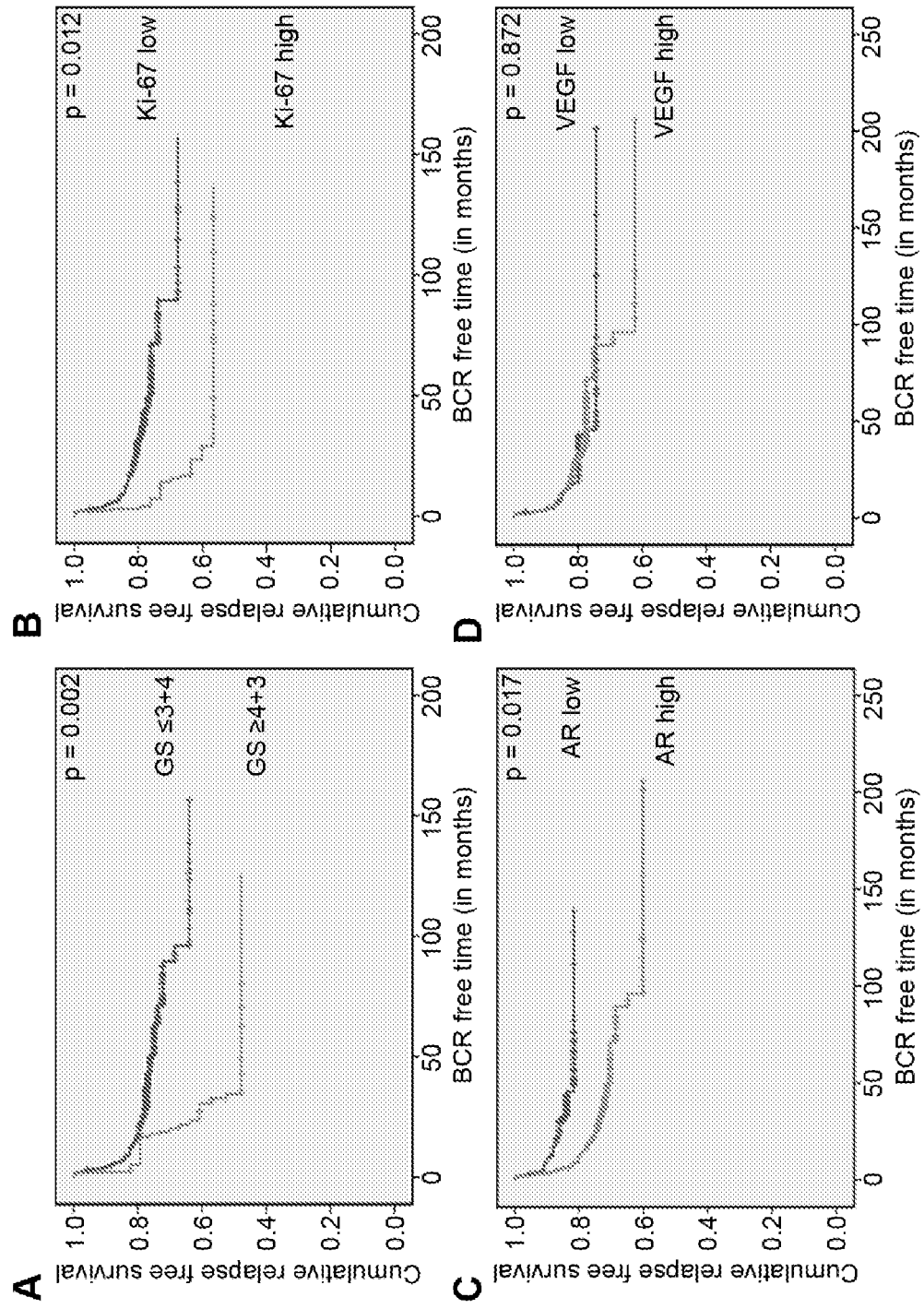
FIG. 5: Validation of the patient material used in this study. A) The patient tumor material was divided into 2 groups based on their Gleason score (GS). As indicated in the panel one group had a Gleason score of ≤3+4 and the other a Gleason score of ≥4+3. Kaplan-Meier curves were then generated for each of the 2 groups with the indicated Gleason scores and their respective BCR free time. B) The panel shows Kaplan-Meier curves plotted between low or high Ki-67 expression and their respective BCR free time. C) The panel shows Kaplan-Meier curves plotted between low or high AR expression and their respective BCR free time. D) The panel shows Kaplan-Meier curves plotted between low or high VEGF expression and their respective BCR free time.
Figure 6:
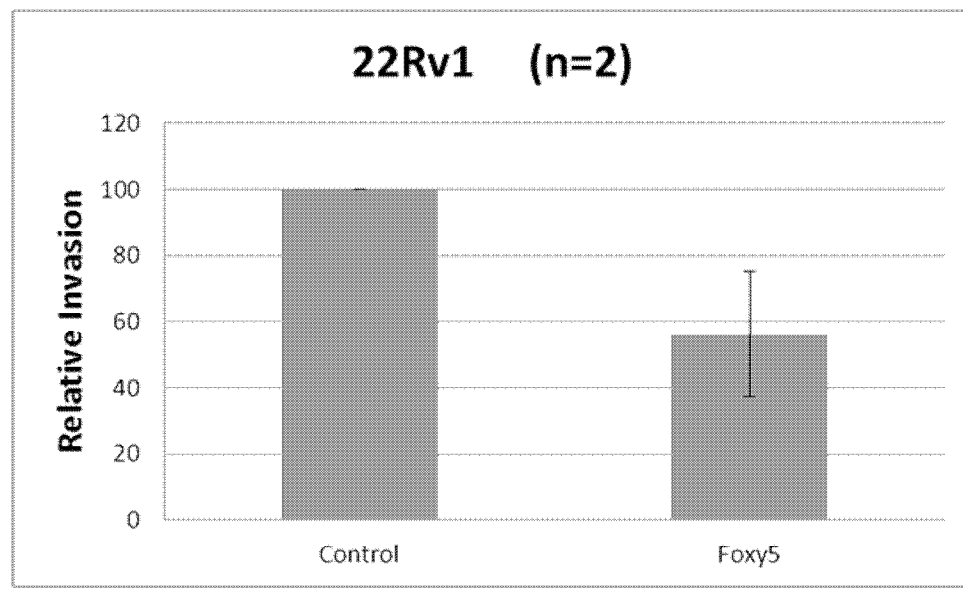
FIG. 6: This figure outlines the invasion of 22Rv1 (A) and DU145 human prostate cells (B) shown to respond to recombinant Wnt5a with a reduction of their invasive capacity (see FIG. 3). The results in this figure show the relative invasion after 24 h in the absence and presence of Foxy-5 (100 microM) in the invasion assay described in the Materials and Methods section. The results are given as means+/−SEM from 2-3 separate experiments.
Figure 6:
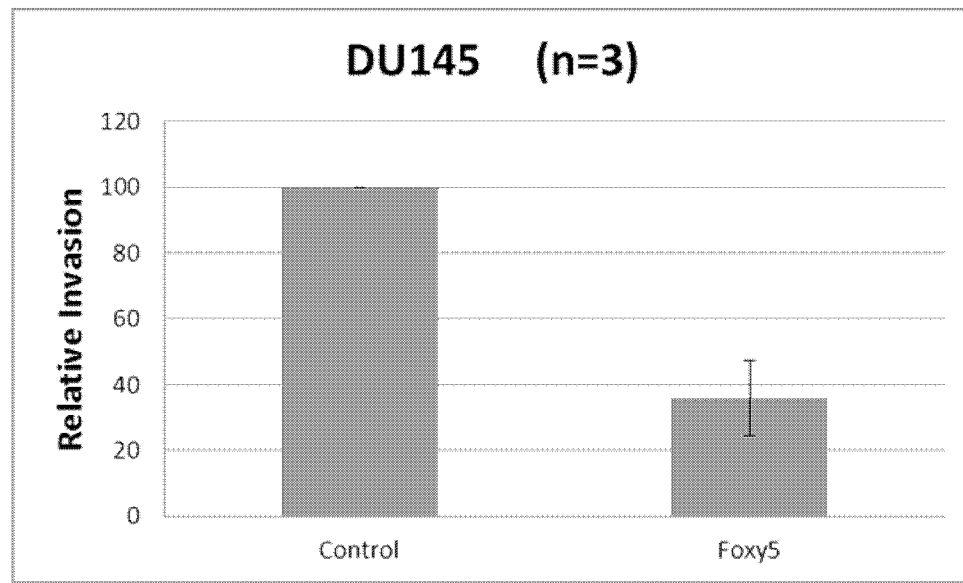

| Factors | Groups | n (%) | Hazard ratio (95% CI) | $\chi^2$ | p - value |
|---|---|---|---|---|---|
| | Wnt5a low VEGF high | 28 (8.3) | 3.501 (1.407-8.712) | | 0.007 |
| | Wnt5a high VEGF high | 219 (64.6) | 1.323 (0.617-2.836) | | 0.472 |
| Path. Gleason Score | ≤3 + 4 | 398 (90.5) | 1 (Reference) | 9.302 | 0.002 |
| | ≥4 + 3 | 42 (9.5) | 2.247 (1.317-3.835) | | |
| Path. T Stage | T2 | 226 (50.4) | 1 (Reference) | 22.05 | 0.0001 |
| | T3 | 222 (49.6) | 2.655 (1.738-4.056) | | | n = Frequency; CI = Confidence Interval; $\chi^2$ = Chi-Square; Path. = Pathological Wnt5a Protein Expression and Prediction of Clinical Outcome Next, the inventors evaluated if Wnt5a protein expression in cancer tissues analyzed after radical prostatectomy for localized PCa could predict clinical outcome as measured by time to biochemical recurrence (BCR), using PSA>0.2 ng/mL in blood samples with a confirmatory value as a surrogate marker. Wnt5a protein expression as illustrated by IHC was significantly higher in cancer areas compared to benign areas (FIG. 1, Table 2). Interestingly, when Kaplan-Meier curve was plotted between Wnt5a protein expression and BCR free time, a favourable outcome (p=0.001) was evident for patients with a high Wnt5a protein expression compared to patients with low Wnt5a protein expression (FIG. 2A). As expected, low expression of AR and of Ki-67 was associated with favorable outcome whereas VEFG expression was not significantly associated with BCR free time (FIG. 5).

Figure 2:
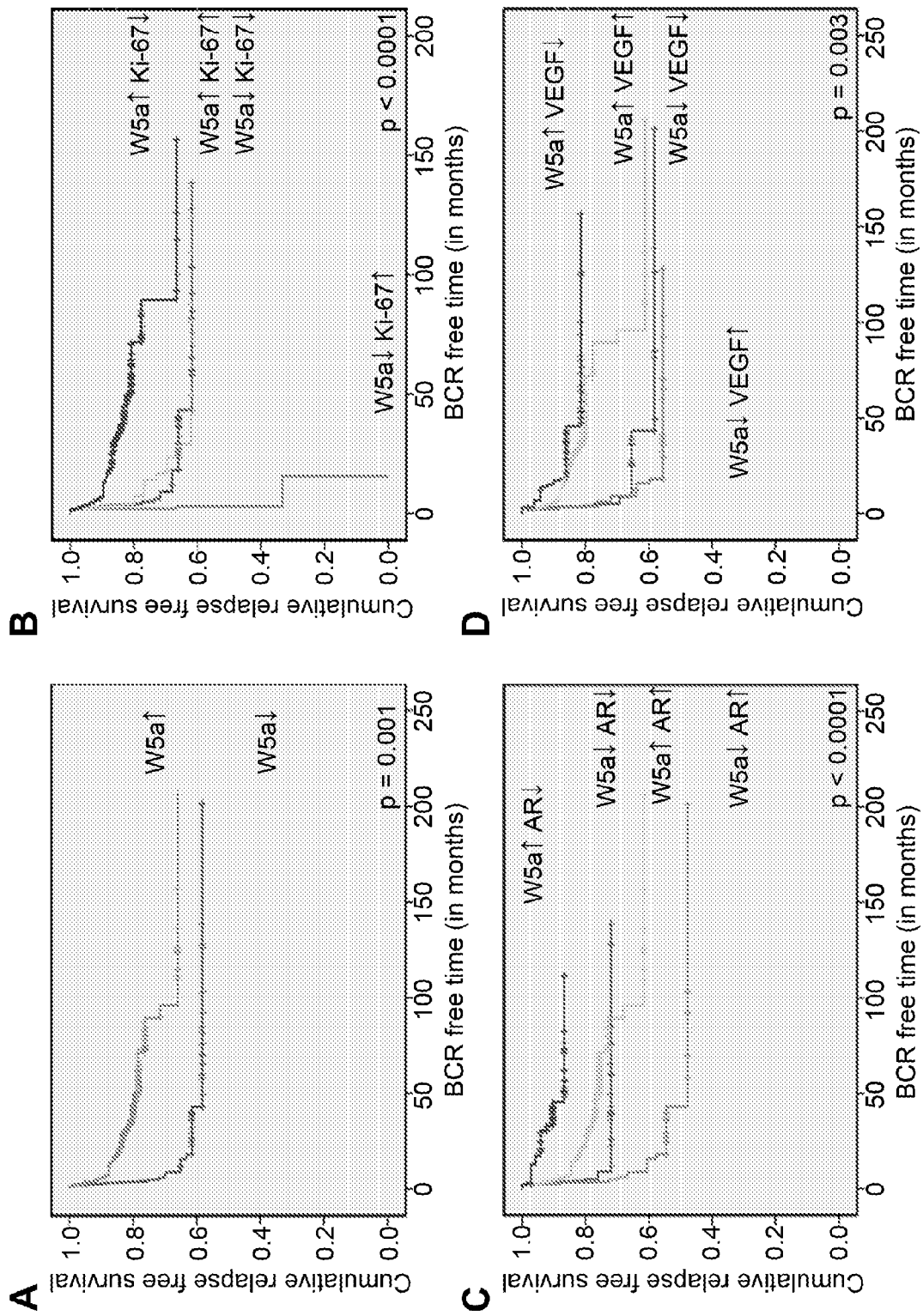
FIG. 2: shows analysis of how Wnt5a protein expression alone or in combination with other biomarkers affects the clinical outcome of PCa patients. All cancer cases were separated into 2 groups based on the staining intensities of Wnt5a, Ki-67, AR and VEGF. The low groups included tumors with scores 0 or 1 and the high groups included tumors with scores 2 or 3. A) The panel shows survival curves plotted between high or low Wnt5a protein expression and BCR free time. B) The panel shows survival curves plotted between high or low Wnt5a and high and low Ki-67 protein expressions. Consequently, the tumors were divided into the following 4 groups; Wnt5a low & Ki-67 low, Wnt5a low & Ki-67 high, Wnt5a high & Ki-67 low and Wnt5a high & Ki-67 high. C) The panel shows survival curves plotted between high or low Wnt5a and high and low AR protein expressions. Consequently, the tumors were divided into the following 4 groups; Wnt5a low & AR low, Wnt5a low & AR high, Wnt5a high & AR low and Wnt5a high & AR high. D) The panel shows survival curves plotted between high or low Wnt5a and high and low VEGF protein expressions. Consequently, the tumors were divided into the following 4 groups; Wnt5a low & VEGF low, Wnt5a low & VEGF high, Wnt5a high & VEGF low and Wnt5a high & VEGF high. In all panels high expression of a protein is indicated by ↑ whereas ↓ indicates low expression. Each step in the curves represent relapse in PCa. The given p-values at the bottom right hand side of the panels indicate significant differences in outcome between the most favorable group and the least favorable group (see Table 4 for more detailed information).

Further, the inventors examined if Wnt5a protein expression also could predict outcome when combined with any of the other tissue biomarkers. The best prediction model was obtained when Wnt5a protein expression was combined with either AR or Ki-67 expression (FIG. 2 B, C), as patients with high Wnt5a and low AR or low Ki-67 expression showed better relapse free survival (p<0.0001), whereas patients with low Wnt5a expression and high AR or high Ki-67 expression had the worst outcome after surgery. Patients with high Wnt5a and low VEGF expression had better outcome compared to other groups (p=0.003) or each marker alone. However, the combination of high Wnt5a and low VEGF was inferior to when Wnt5a was analyzed in combination with AR or Ki-67 indicating that VEGF in not as strong as AR or Ki-67 to predict outcome in combination with Wnt5a in the present context (FIG. 2 D). Cox regressional analysis was used for multivariate analyses and revealed that Wnt5a expression, Gleason score and pathological T stage were independent factors influencing relapse free survival in PCa (Table 4).

Wnt5a Protein Expression and its Effects on Invasion of PCa Cell Lines

Figure 3:
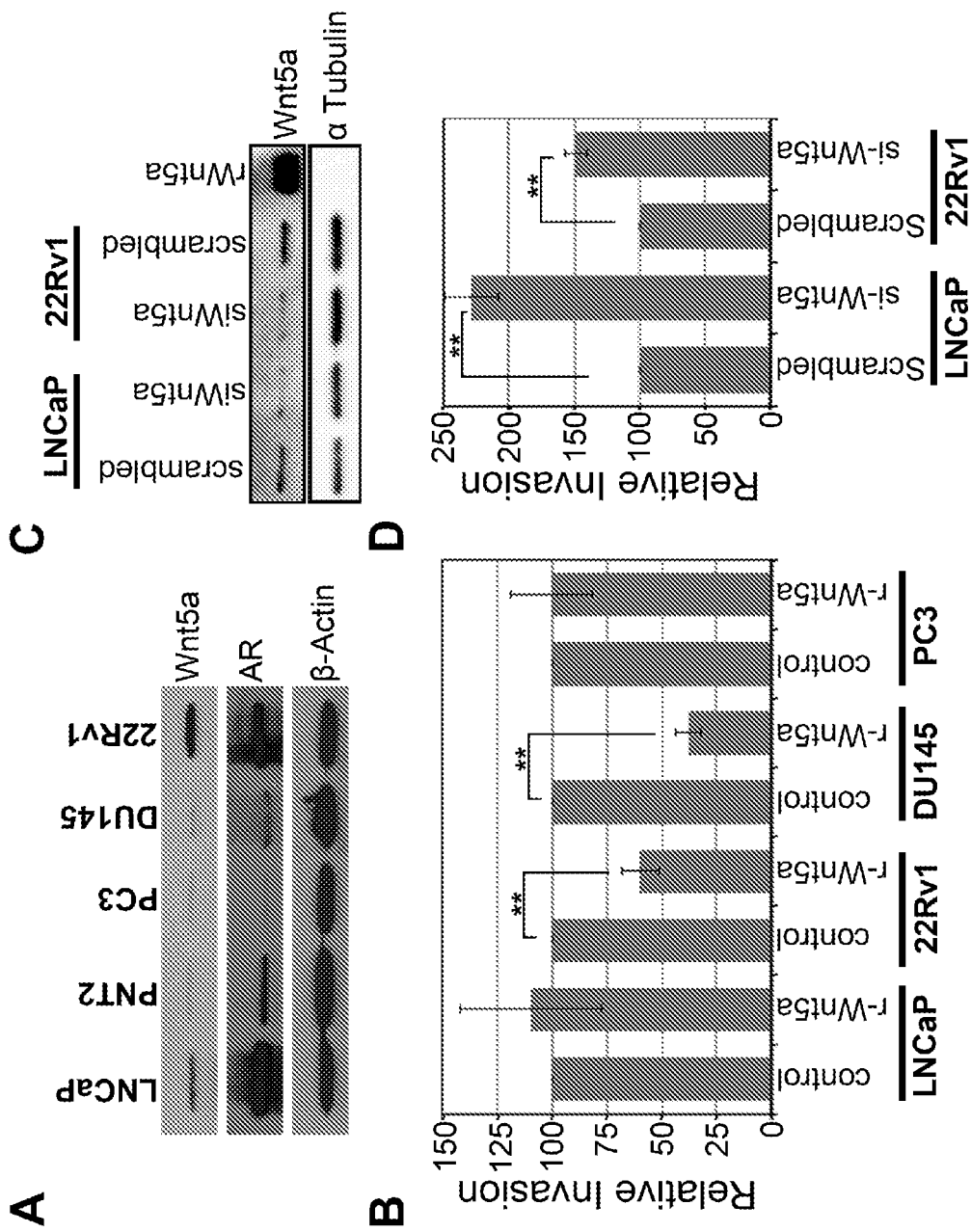
FIG. 3: shows analysis of Wnt5a protein expression in different prostate cell lines and its effect on PCa cell invasiveness. A) This panel shows the endogenous Wnt5a and AR expression in four indicated PCa cell lines (LNCaP, 22Rv1, DU145 and PC3 cells) and in one immortalized human prostate epithelial cell line (PNT2 cells). Wnt5a protein band was identified by running rWnt5a in parallel on the same gel. The blots were reprobed for β-actin as loading control. The presented blots are representative of 4 separate experiments. B) The panel outlines the relative invasion of LNCaP, 22Rv1, DU145 and PC3 cell lines after 24 h in the absence or presence of rWnt5a (0.4 μg/ml) in the assay described in the Materials and Methods section. The results are given as means±SEM from 5 separate experiments. The differences in invasion between cells treated with vehicle alone or with rWnt5a were evaluated for statistical significance (p=0.0001 for 22Rv1 and p<0.0001 for DU145). C) The panel depicts the effects of siRNA knockdown of Wnt5a in LNCaP and 22Rv1. The blots were reprobed for α-tubulin as loading control. The presented blots are representative of 4 separate experiments. D) The panel outlines the relative invasion of LNCaP and 22Rv1 cells after treatment with Wnt5a si-RNA (Wnt5a knockdown) or scrambled siRNA (control), in the same assay previously used in panel B. The results are given as means±SEM from 5 separate experiments. The difference in invasion between scrambled and si-Wnt5a knocked down cells were statistically significant for both cell lines (p<0.0001).

The data of the inventors show that patients with high Wnt5a protein expression have more favorable outcome compared to patients with low Wnt5a protein expression. To better understand this finding Wnt5a protein expression in one SV40 immortalized normal human prostate epithelial cell line (PNT2) and four different PCa cell lines were examined. PNT2 cells had a low expression of endogenous Wnt5a protein whereas there was considerable Wnt5a expression in the PCa cell lines LNCaP and 22Rv1 (FIG. 3 A). These data are in good agreement with the findings of Wnt5a protein expression in the presently analyzed cohort of PCa and a recent study also performed on normal prostate epithelial and PCa cell lines [26]. However, analyses of the two more aggressive PCa cell lines (PC3 and DU145) revealed very low expression of Wnt5a protein, comparable to that of the normal PNT2 prostate epithelial cell line (FIG. 3 A). Interestingly enough, the Wnt5a protein levels matched with the AR protein expressions in these cell lines (FIG. 3 A).

The inventors used the four cancer cell lines (LNCaP, 22Rv1, PC3 and DU145) for the subsequent invasion experiments. Addition of recombinant Wnt5a (rWnt5a) decreased the invasive behavior of both 22Rv1 and DU145 cancer cells (FIG. 3 B). Neither the LNCaP nor the PC3 cells did respond to rWnt5a with a change in their invasive behavior. The result with the PC3 cells is in accordance to a recently published report by Wang et al [26], in which PC3 cells did not respond to addition of rWnt5a in a migration wound scratch assay. LNCaP cells are known to have a very low invasion activity, and this might explain why these cells did not respond when rWnt5a was added. However, when Wnt5a expression in LNCaP cells was knocked down using si-RNAs (FIG. 3 C), there was a significant increase in the invasive behavior of LNCaP cells (FIG. 3 D). In addition, Wnt5a knockdown by si-RNA in 22Rv1 cancer cells also resulted in increased invasion of these cells (FIGS. 3 C and 3 D).

DISCUSSION

To the knowledge of the inventors, only one study with a limited number of patients has up until now demonstrated a role of Wnt5a protein to predict clinical outcome in PCa [25]. This urged the inventors to perform a study on Wnt5a protein expression in a larger cohort of well-defined PCa patients with localized and predominantly low-grade disease and relate the results with the expression of other known tissue biomarkers and most importantly with BCR. The present study involved a consecutive series of PCa patients that had undergone radical prostatectomy during 1988-2003 at Skåne University Hospital, Malmö, Sweden with a mean follow-up time of 41.6 month (range 1.51-205.90). This patient cohort is large, population based, and the patients are well characterized (Table 1). In the TMA slides benign and malignant tissues from the same patient are present in duplicates. Based on Gleason grades patient material was further characterized into low-grade cancers (Gleason score up to 3+4) and high-grade cancers (Gleason 4+3 or higher). Almost 89% of the patients were classified as low-grade cancers, which is to be expected in a group of patients with localized PCa suitable for radical prostatectomy. As a control of the clinical material, the inventors ascertained that there was a statistically significant difference in clinical outcome between patients with low-grade and high-grade cancer using Kaplan-Meier analyses of BCR free survival (FIG. 5 A). Further control of the clinical material also revealed that the same was true when proliferation was studied by Ki-67 expression, a validated tissue biomarker in PCa [30]. Patients with high Ki-67 expression had reduced relapse free survival time when compared with patients with a low number of Ki-67 expressing tumor cells (FIG. 5 B).

In the present TMA study the inventors clearly show that Wnt5a protein expression was increased in localized PCa when compared to benign tissue from the same patients, an effect that exhibited a strong statistical significance ($p<0.0001$; FIGS. 1 A, B and G, Table 2). These results are in good agreement with the recent findings obtained from a smaller cohort [25]. The clinical conclusion that Wnt5a protein expression is increased in localized PCa tissue compared with normal/benign tissue is also supported by the analysis of different human prostate cell lines. The inventors clearly observed that the PNT2 cell line, an SV40 immortalized cell line derived from normal human prostate epithelium express very low levels of endogenous Wnt5a protein, whereas the expression of Wnt5a protein was high in the PCa cell lines LNCaP and 22Rv1. The more aggressive cell lines, PC3 and DU145, had a very low Wnt5a protein expression. This is in line with the less favorable outcome observed in Wnt5 low tumors. However, in the TMA material, Wnt5a was not down-regulated in the high-grade (Gleason score≥4+3) PCa cases. If these seemingly contradicting results indicate a grade-unrelated function of Wnt5a or only reflect the individual characteristics of the two tumors from which the cell lines were derived is hard to say. As an alternative explanation, the number of high-grade PCa in the present cohort (n=41) might be too small to detect a grade-related Wnt5a down-regulation.

The inventors also found increased expression of AR, Ki-67 and VEGF proteins in localized PCa tissue compared to benign tissue (FIG. 1 C-F, H-I, Table 2). To obtain a first insight into possible mechanisms for how Wnt5a functions in PCa, the inventors performed statistical analyses of potential correlations between Wnt5a protein expression and that of AR, Ki-67 and VEGF, all three well known to be upregulated in progressive PCa. Wnt5a significantly correlated with VEGF, a marker for angiogenesis, indicating that Wnt5a might be related to tumor growth (Table 3). In this regard the present data is somewhat different from those reported from analyses of non-small cell lung cancer where Wnt5a did not correlate with VEGF expression in the cancer tissue but with VEGF in the surrounding stromal tissue [31]. Furthermore, Wnt5a expression in PCa tissue in this study is weakly but significantly associated with AR expression (Table 3). Protein expression analysis by western blot indicated that Wnt5a levels and AR expression in one immortalized prostate epithelial cell line and 4 different PCa cell lines matched with each other, indicating a possible correlation between Wnt5a and AR in PCa (FIG. 3 A). Despite these data, it has been recently shown that Wnt5a inhibits AR transcriptional activity in 22Rv1 cells when these cells were transfected with a Wnt5a plasmid [32]. Finally, Wnt5a protein expression was weakly but significantly associated with Ki-67 expression (Table 3). This result is in accordance with the report on Non-small-cell lung cancer, where intratumoral Wnt5a expression significantly correlated with Ki-67 proliferation index [31], but in contrast to the study on hepatocellular carcinoma where Wnt5a has a tumor suppressing effect and loss of Wnt5a has a strong correlation with high Ki-67 proliferation index [33]. Taken together these data indicate that the role of Wnt5a signaling in the regulation of tumor cell proliferation is uncertain.

In the present investigation the inventors did not find a correlation between Wnt5a protein expression and the Gleason score, although the latter may be the best available prognostic indicator of outcome in PCa [34]. However, Gleason scoring has its limitations due to interobserver variability among pathologists and hence there is a need for complementary markers. To determine whether or not Wnt5a protein expression can be used to predict outcome (relapse-free survival) after surgery in patients with localized PCa in this population-based cohort, Kaplan-Meier curves were plotted between Wnt5a protein expression and BCR free time (FIG. 2 A). Interestingly, patients with high Wnt5a protein expression had a statistically significant more favorable outcome compared to patients with low Wnt5a protein expression indicating that the Wnt5a 306 protein has a tumor suppressive function in the context of localized PCa. In majority of cases, Wnt5a signaling has opposite effects than Wnt/β-catenin signaling, for example in malignant melanoma [35]. Although a different and more advanced PCa patient material was used by Chen and co-workers, their finding that Wnt1 and β-catenin expression can serve as markers for PCa progression [12] is compatible with the data that Wnt5a predicts a more favorable outcome in PCa patients.

Combining Wnt5a protein expression with other well-known PCa markers could further improve the predictive power of Wnt5a as previously mentioned. The hypothesis that Wnt5a has a tumor suppressive function was further supported by the invasion data in three of four PCa cell lines investigated. Addition of rWnt5a led to decrease in invasion in 22Rv1 and DU145 cells. It was not surprising that LNCaP cells, known to have a very low invasive behavior, did not exhibit a detectable further reduction in its invasive behavior in response to rWnt5a. However, Wnt5a knockdown experiments were performed on LNCaP cells, as well as on 22Rv1 cells, Wnt5a siRNAs increased the invasive activity of LNCaP and 22Rv1 cells; indicating that for PCa cells to invade, Wnt5a must be actively silenced.

It has recently been suggested that Wnt5a promotes aggressiveness of PCa and patients with low/negative Wnt5a expression have better relapse free survival after radical prostatectomy [25]. These results are quite in contrast to the present findings. Their contrasting results can be attributed to less patient samples and the fact that in their material 24.5% (24 out of 98 patients) of the tumors had a Gleason score of 8 or higher, whereas in the study leading to the invention only 11% of the tumors had such a high Gleason score. Furthermore, different Wnt5a antibodies were used in the two studies. The Wnt5a antibody has been evaluated by peptide blocking experiments during IHC [20], loss of Wnt5a following siRNA knockdown and Wnt5a overexpression. However, it cannot be excluded that Wnt5a exerts different effects on tumor progression in different stages of the disease. The different results from the in vitro invasion assay can possibly be explained by the fact that the inventors have used a defined concentration of rWnt5a and the other group used cells transfected to overexpress Wnt5a without any control of the actual stimulating concentration of Wnt5a.

There are studies within the scientific community on the possible role of Wnt5a in suppressing or promoting tumor progression. It must be pointed out that an upregulation of Wnt5a mRNA in a specific cancer type does not alone indicate a tumor promoting function, since this might very well go hand in hand with a reduced Wnt5a protein level. Even if this is taken into account it appears as if Wnt5a has different functions in different types of tumors [16]. In conclusion, this study indicates that although Wnt5a protein expression is elevated in PCa, its expression in PCa cells is associated with a more favorable outcome for patients with localized disease. One important mechanism for such an effect of Wnt5a in PCa progression is the present demonstration that Wnt5a can impair the invasive behavior of PCa cells in vitro. Taken together, these results suggest a novel therapeutic approach for patients with localized PCa by targeting Wnt5a to impair progression of PCa in these patients.

REFERENCES

1. Jemal A, Siegel R, Xu J, Ward E (2010) Cancer statistics, 2010. CA Cancer J Clin 60: 277-300.
2. Heinlein C A, Chang C (2004) Androgen receptor in prostate cancer. Endocr Rev 25: 276-308.
3. Feldman B J, Feldman D (2001) The development of androgen-independent prostate cancer. Nat Rev Cancer 1: 34-45.
4. Chen C D, Welsbie D S, Tran C, Baek S H, Chen R, et al. (2004) Molecular determinants of resistance to antiandrogen therapy. Nat Med 10: 33-39.
5. Debes J D, Tindall D J (2004) Mechanisms of androgen-refractory prostate cancer. N Engl J Med 351: 1488-1490.
6. Chesire D R, Ewing C M, Gage W R, Isaacs W B (2002) In vitro evidence for complex modes of nuclear beta-catenin signaling during prostate growth and tumorigenesis. Oncogene 21:2679-2694.
7. Truica C I, Byers S, Gelmann E P (2000) Beta-catenin affects androgen receptor transcriptional activity and ligand specificity. Cancer Res 60: 4709-4713.
8. Nusse R, Brown A, Papkoff J, Scambler P, Shackleford G, et al. (1991) A new nomenclature for int-1 and related genes: the Wnt gene family. Cell 64: 231.
9. Cadigan K M, Nusse R (1997) Wnt signaling: a common theme in animal development. Genes Dev 11: 3286-3305.
10. Logan C Y, Nusse R (2004) The Wnt signaling pathway in development and disease. Annu Rev Cell Dev Biol 20: 781-810.
11. Tsukamoto A S, Grosschedl R, Guzman R C, Parslow T, Varmus H E (1988) Expression of the int-1 gene in transgenic mice is associated with mammary gland hyperplasia and adenocarcinomas in male and female mice. Cell 55: 619-625.
12. Chen G, Shukeir N, Potti A, Sircar K, Aprikian A, et al. (2004) Up-regulation of Wnt-1 and beta-catenin production in patients with advanced metastatic prostate carcinoma: potential pathogenetic and prognostic implications. Cancer 101: 1345-1356.
13. Iozzo R V, Eichstetter I, Danielson K G (1995) Aberrant expression of the growth factor Wnt-5A in human malignancy. Cancer Res 55: 3495-3499.
14. Qian D, Jones C, Rzadzinska A, Mark S, Zhang X, et al. (2007) Wnt5a functions in planar cell polarity regulation in mice. Dev Biol 306: 121-133.
15. Slusarski D C, Yang-Snyder J, Busa W B, Moon R T (1997) Modulation of embryonic intracellular Ca2+ signaling by Wnt-5A. Dev Biol 182: 114-120.
16. McDonald S L, Silver A (2009) The opposing roles of Wnt-5a in cancer. Br J Cancer 101: 209-214.
17. Dejmek J, Dejmek A, Safholm A, Sjolander A, Andersson T (2005) Wnt-5a protein expression in primary dukes B colon cancers identifies a subgroup of patients with good prognosis. Cancer Res 65: 9142-9146.
18. Blanc E, Roux G L, Benard J, Raguenez G (2005) Low expression of Wnt-5a gene is associated with high-risk neuroblastoma. Oncogene 24: 1277-1283.
19. Dejmek J, Leandersson K, Manjer J, Bjartell A, Emdin S O, et al. 533 (2005) Expression and signaling activity of Wnt-5a/discoidin domain receptor-1 and Syk plays distinct but decisive roles in breast cancer patient survival. Clin Cancer Res 11: 520-528.
20. Jonsson M, Dejmek J, Bendahl P O, Andersson T (2002) Loss of Wnt-5a protein is associated with early relapse in invasive ductal breast carcinomas. Cancer Res 62: 409-416.
21. Liang H, Chen Q, Coles A H, Anderson S J, Pihan G, et al. (2003) Wnt5a inhibits B cell proliferation and functions as a tumor suppressor in hematopoietic tissue. Cancer Cell 4: 349-360.
22. Fernandez-Cobo M, Zammarchi F, Mandeli J, Holland J F, Pogo B G (2007) Expression of Wnt5A and Wnt10B in non-immortalized breast cancer cells. Oncol Rep 17: 903-907.
23. Kurayoshi M, Oue N, Yamamoto H, Kishida M, Inoue A, et al. (2006) Expression of Wnt-5a is correlated with aggressiveness of gastric cancer by stimulating cell migration and invasion. Cancer Res 66: 10439-10448.
24. Da Forno P D, Pringle J H, Hutchinson P, Osborn J, Huang Q, et al. (2008) WNT5A expression increases during melanoma progression and correlates with outcome. Clin Cancer Res 14: 5825-5832.
25. Yamamoto H, Oue N, Sato A, Hasegawa Y, Matsubara A, et al. (2010) Wnt5a signaling is involved in the aggressiveness of prostate cancer and expression of metalloproteinase. Oncogene 29: 2036-2046.
26. Wang Q, Symes A J, Kane C A, Freeman A, Nariculam J, et al. (2010) A novel role for Wnt/$Ca_{2+}$ 553 signaling in actin cytoskeleton remodeling and cell motility in prostate cancer. PLoS One 5: e10456.
27. Thiele S, Rauner M, Goettsch C, Rachner T D, Benad P, et al. (2011) Expression profile of WNT molecules in prostate cancer and its regulation by aminobisphonates. J Cell Biochem (e-published ahead of print).
28. Wang Q, Williamson M, Bott S, Brookman-Amissah N, Freeman A, et al. (2007) Hypomethylation of WNT5A, CRIP1 and S100P in prostate cancer. Oncogene 26: 6560-6565.
29. Leandersson K, Riesbeck K, Andersson T (2006) Wnt-5a mRNA translation is suppressed by the Elav-like protein HuR in human breast epithelial cells. Nucleic Acids Res 34: 3988-3999.
30. Berney D M, Gopalan A, Kudahetti S, Fisher G, Ambroisine L, et al. (2009) Ki-67 and outcome in clinically localised prostate cancer: analysis of conservatively treated prostate cancer patients from the Trans-Atlantic Prostate Group study. Br J Cancer 100: 888-893.
31. Huang C L, Liu D, Nakano J, Ishikawa S, Kontani K, et al. (2005) Wnt5a expression is associated with the tumor proliferation and the stromal vascular endothelial growth factor—an expression in non-small-cell lung cancer. J Clin Oncol 23: 8765-8773.
32. Kawano Y, Diez S, Uysal-Onganer P, Darrington R S, Waxman J, et al. (2009) Secreted Frizzled-related protein-1 is a negative regulator of androgen receptor activity in prostate cancer. Br J Cancer 100: 1165-1174.
33. Liu X H, Pan M H, Lu Z F, Wu B, Rao Q, et al. (2008) Expression of Wnt-5a and its clinicopathological significance in hepatocellular carcinoma. Dig Liver Dis 40: 560-567.
34. Humphrey P A (2004) Gleason grading and prognostic factors in carcinoma of the prostate. Mod Pathol 17: 292-306.
35. Chien A J, Moore E C, Lonsdorf A S, Kulikauskas R M, Rothberg B G, et al. (2009) Activated Wnt/beta-catenin signaling in melanoma is associated with decreased proliferation in patient tumors and a murine melanoma model. Proc 579 Natl Acad Sci USA 106: 1193-1198.
36. Wegiel B, Bjartell A, Tuomela J, Dizeyi N, Tinzl M, et al. (2008) Multiple cellular mechanisms related to cyclin A1 in prostate cancer invasion and metastasis. J Natl Cancer Inst 100: 1022-1036.

The invention claimed is:

1. A method for treating prostate cancer, the method comprising administering a Wnt5a peptide to a patient in need of said treatment, wherein said Wnt5a peptide is selected from the group consisting of SEQ ID NOs: 1 and 3-16, and formylated derivatives thereof.

2. The method of claim 1, wherein said prostate cancer is caused by cancer cells with low Wnt5a protein expression.

3. The method of claim 1, wherein said prostate cancer is a localized prostate cancer.

4. The method of claim 1, wherein said patient has undergone or will undergo radiation therapy and/or radical prostatectomy.

5. The method of claim 1, wherein said Wnt5a peptide is a recombinant peptide.

6. The method of claim 1, wherein said Wnt5a peptide is selected from the group consisting of SEQ ID NOs: 2-16, and formylated derivatives thereof.

7. The method of claim 6, wherein said Wnt5a peptide is SEQ ID NO: 2, or a formylated derivative thereof.

* * * * *

SEQUENCE LISTING

```
<160> NUMBER OF SEQ ID NOS: 16

<210> SEQ ID NO 1
<211> LENGTH: 6
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa in position 1 is methionine or nor-leucin
<220> FEATURE:
<221> NAME/KEY: MISC_FEATURE
<222> LOCATION: (4)..(4)
<223> OTHER INFORMATION: Xaa in position 4 is cysteine or alanine

<400> SEQUENCE: 1

Xaa Asp Gly Xaa Glu Leu
1               5

<210> SEQ ID NO 2
<211> LENGTH: 6
<212> TYPE: PRT
<213> ORGANISM: Homo sapiens

<400> SEQUENCE: 2

Met Asp Gly Cys Glu Leu
1               5

<210> SEQ ID NO 3
<211> LENGTH: 7
<212> TYPE: PRT
<213> ORGANISM: Homo sapiens

<400> SEQUENCE: 3

Gly Met Asp Gly Cys Glu Leu
1               5

<210> SEQ ID NO 4
<211> LENGTH: 8
<212> TYPE: PRT
<213> ORGANISM: Homo sapiens

<400> SEQUENCE: 4

Glu Gly Met Asp Gly Cys Glu Leu
1               5

<210> SEQ ID NO 5
<211> LENGTH: 9
<212> TYPE: PRT
<213> ORGANISM: Homo sapiens

<400> SEQUENCE: 5

Ser Glu Gly Met Asp Gly Cys Glu Leu
1               5

<210> SEQ ID NO 6
<211> LENGTH: 10
<212> TYPE: PRT
<213> ORGANISM: Homo sapiens

<400> SEQUENCE: 6

Thr Ser Glu Gly Met Asp Gly Cys Glu Leu
1               5                   10

<210> SEQ ID NO 7
<211> LENGTH: 11
```

```
<212> TYPE: PRT
<213> ORGANISM: Homo sapiens

<400> SEQUENCE: 7

Lys Thr Ser Glu Gly Met Asp Gly Cys Glu Leu
1               5                   10

<210> SEQ ID NO 8
<211> LENGTH: 12
<212> TYPE: PRT
<213> ORGANISM: Homo sapiens

<400> SEQUENCE: 8

Asn Lys Thr Ser Glu Gly Met Asp Gly Cys Glu Leu
1               5                   10

<210> SEQ ID NO 9
<211> LENGTH: 13
<212> TYPE: PRT
<213> ORGANISM: Homo sapiens

<400> SEQUENCE: 9

Cys Asn Lys Thr Ser Glu Gly Met Asp Gly Cys Glu Leu
1               5                   10

<210> SEQ ID NO 10
<211> LENGTH: 14
<212> TYPE: PRT
<213> ORGANISM: Homo sapiens

<400> SEQUENCE: 10

Leu Cys Asn Lys Thr Ser Glu Gly Met Asp Gly Cys Glu Leu
1               5                   10

<210> SEQ ID NO 11
<211> LENGTH: 15
<212> TYPE: PRT
<213> ORGANISM: Homo sapiens

<400> SEQUENCE: 11

Arg Leu Cys Asn Lys Thr Ser Glu Gly Met Asp Gly Cys Glu Leu
1               5                   10                  15

<210> SEQ ID NO 12
<211> LENGTH: 16
<212> TYPE: PRT
<213> ORGANISM: Homo sapiens

<400> SEQUENCE: 12

Gly Arg Leu Cys Asn Lys Thr Ser Glu Gly Met Asp Gly Cys Glu Leu
1               5                   10                  15

<210> SEQ ID NO 13
<211> LENGTH: 17
<212> TYPE: PRT
<213> ORGANISM: Homo sapiens

<400> SEQUENCE: 13

Gln Gly Arg Leu Cys Asn Lys Thr Ser Glu Gly Met Asp Gly Cys Glu
1               5                   10                  15

Leu

<210> SEQ ID NO 14
<211> LENGTH: 18
```

```
<212> TYPE: PRT
<213> ORGANISM: Homo sapiens

<400> SEQUENCE: 14

Thr Gln Gly Arg Leu Cys Asn Lys Thr Ser Glu Gly Met Asp Gly Cys
1               5                   10                  15

Glu Leu

<210> SEQ ID NO 15
<211> LENGTH: 19
<212> TYPE: PRT
<213> ORGANISM: Homo sapiens

<400> SEQUENCE: 15

Gly Thr Gln Gly Arg Leu Cys Asn Lys Thr Ser Glu Gly Met Asp Gly
1               5                   10                  15

Cys Glu Leu

<210> SEQ ID NO 16
<211> LENGTH: 20
<212> TYPE: PRT
<213> ORGANISM: Homo sapiens

<400> SEQUENCE: 16

Leu Gly Thr Gln Gly Arg Leu Cys Asn Lys Thr Ser Glu Gly Met Asp
1               5                   10                  15

Gly Cys Glu Leu
            20
```